US009539403B2

(12) United States Patent
Eves et al.

(10) Patent No.: US 9,539,403 B2
(45) Date of Patent: Jan. 10, 2017

(54) MASK SYSTEM

(75) Inventors: Matthew Eves, Manly Vale (AU);
Muditha Pradeep Dantanarayana, Cherrybrook (AU); Errol Savio Alex D'Souza, Hornsby Heights (AU); Rupert Christian Scheiner, Davidson (AU); Stuart Norris Plascott, Macquarie Park (AU); Jamie Graeme Wehbeh, Mosman (AU); Murray William Lee, Quakers Hill (AU)

(73) Assignee: ResMed Limited, Bella Vista (AU)

( * ) Notice: Subject to any disclaimer, the term of this patent is extended or adjusted under 35 U.S.C. 154(b) by 1209 days.

(21) Appl. No.: 13/390,639

(22) PCT Filed: Aug. 26, 2009

(86) PCT No.: PCT/AU2009/001102
§ 371 (c)(1),
(2), (4) Date: Feb. 15, 2012

(87) PCT Pub. No.: WO2011/022751
PCT Pub. Date: Mar. 3, 2011

(65) Prior Publication Data
US 2012/0138063 A1 Jun. 7, 2012

(51) Int. Cl.
*A61M 16/06* (2006.01)
(52) U.S. Cl.
CPC ......... *A61M 16/06* (2013.01); *A61M 16/0633* (2014.02); *A61M 16/0683* (2013.01)
(58) Field of Classification Search
CPC ..... A61M 16/06; A61M 16/0683; A62B 9/04; A62B 18/084; A62B 18/02; A61F 9/02; A63B 33/002; B63C 11/12; A41D 13/1161

USPC ........... 128/206.21, 206.27, 206.28, 207.11, 128/207.13, 207.15, 207.17; 403/326, 403/329, 409.1
See application file for complete search history.

(56) References Cited

U.S. PATENT DOCUMENTS

| 2,127,136 A | 8/1938 | Pobirs |
| 2,540,567 A * | 2/1951 | Bennett ................. A61M 16/06 128/206.26 |
| 2,837,090 A | 6/1958 | Bloom et al. |
| 4,850,346 A | 7/1989 | Michel et al. |
| 5,488,948 A * | 2/1996 | Dubruille ............. A62B 18/084 128/206.21 |

(Continued)

FOREIGN PATENT DOCUMENTS

| EP | 1 057 494 | 12/2000 |
| WO | WO 97/20597 | 6/1997 |

(Continued)

OTHER PUBLICATIONS

U.S. Appl. No. 14/447,673, filed Jul. 31, 2014.
(Continued)

*Primary Examiner* — Justine Yu
*Assistant Examiner* — Douglas Sul
(74) *Attorney, Agent, or Firm* — Nixon & Vanderhye P.C.

(57) ABSTRACT

A mask system (10) includes a frame (20) defining a breathing chamber, a cushion (40) provided to the frame and adapted to form a seal with the patient's face, and a shroud (50) provided to the frame and adapted to attach headgear. The shroud includes a retaining mechanism structured to connect the shroud to the frame. The retaining mechanism includes both a taper lock arrangement and a retaining clip arrangement.

29 Claims, 52 Drawing Sheets

(56) References Cited

U.S. PATENT DOCUMENTS

| | | | |
|---|---|---|---|
| 5,517,986 A * | 5/1996 | Starr et al. | 128/206.24 |
| 5,921,239 A | 7/1999 | McCall et al. | |
| 6,039,044 A | 3/2000 | Sullivan | |
| 6,371,110 B1 * | 4/2002 | Peterson | A62B 18/084 128/202.27 |
| 7,353,827 B2 * | 4/2008 | Geist | A61M 16/06 128/206.21 |
| 7,370,652 B2 * | 5/2008 | Matula, Jr. | A61M 16/06 128/206.11 |
| 7,900,630 B2 | 3/2011 | Geiselhart et al. | |
| 8,522,784 B2 | 9/2013 | Ng et al. | |
| 8,528,561 B2 | 9/2013 | Ng et al. | |
| 8,550,084 B2 | 10/2013 | Ng et al. | |
| 2002/0117177 A1 * | 8/2002 | Kwok | 128/207.11 |
| 2004/0112384 A1 * | 6/2004 | Lithgow | A61M 16/06 128/206.21 |
| 2006/0042629 A1 | 3/2006 | Geist | |
| 2006/0118117 A1 * | 6/2006 | Berthon-Jones et al. | 128/206.21 |
| 2006/0260614 A1 | 11/2006 | Biener et al. | |
| 2006/0272646 A1 | 12/2006 | Ho et al. | |
| 2006/0283461 A1 * | 12/2006 | Lubke | A61M 16/06 128/207.11 |
| 2007/0044804 A1 | 3/2007 | Matula et al. | |
| 2007/0157353 A1 | 7/2007 | Guney et al. | |
| 2008/0178875 A1 | 7/2008 | Henry | |
| 2009/0050156 A1 | 2/2009 | Ng et al. | |
| 2010/0012128 A1 * | 1/2010 | Takishita et al. | 128/206.24 |
| 2013/0133660 A1 | 5/2013 | Ng et al. | |
| 2013/0327333 A1 | 12/2013 | Ng et al. | |

FOREIGN PATENT DOCUMENTS

| | | |
|---|---|---|
| WO | WO 2004/096332 | 11/2004 |
| WO | WO 2005/021075 | 3/2005 |
| WO | WO 2005/063326 | 7/2005 |
| WO | WO 2005/063327 | 7/2005 |
| WO | WO 2005/123166 | 12/2005 |
| WO | WO 2006/000046 | 1/2006 |
| WO | WO 2006069415 A1 * | 7/2006 |
| WO | WO 2006/133012 | 12/2006 |
| WO | WO 2007/041751 | 4/2007 |
| WO | WO 2007/045008 | 4/2007 |
| WO | WO 2007/048174 | 5/2007 |
| WO | WO 2007/053878 | 5/2007 |
| WO | WO 2008/058330 | 5/2008 |
| WO | WO 2009/108995 | 9/2009 |
| WO | WO 2009/108995 | 11/2009 |

OTHER PUBLICATIONS

Photographs of Weinmann Mask, acquired prior to 1998, 7 pages.
International Search Report for PCT/AU2009/001102 mailed (Dec. 11, 2009).

* cited by examiner

MASK SYSTEM

This application is the U.S. national phase of International Application No. PCT/AU2009/001102 filed 26 Aug. 2009 which designated the U.S., the entire contents of which are hereby incorporated by reference.

FIELD OF THE INVENTION

The present invention relates to a mask system used for treatment, e.g., of Sleep Disordered Breathing (SDB) with Continuous Positive Airway Pressure (CPAP) or Non-Invasive Positive Pressure Ventilation (NIPPV).

BACKGROUND OF THE INVENTION

Patient interfaces, such as a full-face or nasal mask systems, for use with positive airway pressure (PAP) devices in the treatment of sleep disordered breathing (SDB), typically include a soft face-contacting portion, such as a cushion, and a rigid or semi-rigid shell or frame. In use, the interface is held in a sealing position by headgear so as to enable a supply of air at positive pressure (e.g., 2-30 cm $H_2O$) to be delivered to the patient's airways.

One factor in the efficacy of therapy and compliance of patients with therapy is the comfort and fit of the patient interface.

The present invention provides alternative arrangements of mask systems to enhance the efficacy of therapy and compliance of patients with therapy.

SUMMARY OF THE INVENTION

One aspect of the invention relates to a mask system including a frame defining a breathing chamber, a cushion provided to the frame and adapted to form a seal with the patient's face, and a shroud provided to the frame and adapted to attach headgear. The shroud includes a retaining mechanism structured to connect the shroud to the frame. The retaining mechanism includes both a taper lock arrangement and a retaining clip arrangement.

Another aspect of the invention relates to headgear for a mask system including a pair of upper straps adapted to connect to an upper portion of the mask system, a pair of lower straps adapted to connect to a lower portion of the mask system, and a cross bar to connect one of the upper straps to one of the lower straps on each side of the patient's head. The cross bar limits relative movement of the upper and lower straps relative one another so as to maintain the upper strap in a position away from the patient's field of vision and allow a force vector applied to upper strap to be directed towards the back of the patient's head in use.

Another aspect of the invention relates to a mask system including a frame defining a breathing chamber, a cushion provided to the frame and adapted to form a seal with the patient's face, and a shroud provided to the frame and adapted to attach headgear. The shroud includes upper headgear connectors adapted to attach upper headgear straps and lower headgear connectors adapted to attach lower headgear straps. Each lower headgear connector includes a clip receptacle adapted to removably interlock with a headgear clip associated with a respective lower headgear strap. Each clip receptacle is connected to the shroud via spaced-apart arm members that allow flexible movement of the clip receptacle in use.

Another aspect of the invention relates to a mask system including a frame defining a breathing chamber, a cushion provided to the frame and adapted to form a seal with the patient's face, and upper headgear connectors adapted to attach upper headgear straps and lower headgear connectors adapted to attach lower headgear straps. Each upper headgear connector includes an elongated arm and a slot at the free end of the arm adapted to receive a respective upper headgear strap and each lower headgear connector includes a clip receptacle adapted to removably interlock with a headgear clip associated with a respective lower headgear strap. The slot is oriented about 2-26° with respect to a vertical axis of the frame.

Another aspect of the invention relates to a mask system including a frame defining a breathing chamber, a cushion provided to the frame and adapted to form a seal with the patient's face, and a shroud provided to the frame and adapted to attach headgear. The shroud includes upper headgear connectors adapted to attach upper headgear straps and lower headgear connectors adapted to attach lower headgear straps. Each lower headgear connector includes a clip receptacle adapted to removably interlock with a headgear clip associated with a respective lower headgear strap. Each clip receptacle is oriented about 2-12° with respect to a vertical axis of the frame.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1-2 is a side view of the mask system of FIG. 1-1;

FIG. 2-1 is a perspective view of the mask system of FIG. 1-1 without headgear;

FIG. 2-2 is a side view of the mask system of FIG. 2-1;

FIG. 3-1 is a side view of the frame and upper headgear connector of the mask system of FIG. 1-1;

FIG. 3-2 is a rear view of the frame and upper headgear connector of FIG. 3-1;

FIG. 4-1 is a perspective view of the frame of the mask system of FIG. 1-1;

FIG. 4-2 is a front view of the frame of FIG. 4-1;

FIG. 4-3 is a side view of the frame of FIG. 4-1;

FIG. 4-4 is a top view of the frame of FIG. 4-1;

FIG. 5-1 is a side view showing different sizes of the frame of FIG. 4-1, in overlapping relation;

FIG. 5-2 is a front view showing different sizes of the frame of FIG. 4-1, in overlapping relation;

FIGS. 6-1 to 6-6 are various views of an upper headgear connector according to an embodiment of the present invention;

FIGS. 7-1 to 7-5 are various views of an upper headgear connector according to an embodiment of the present invention;

FIG. 8-1 is a top view showing different sizes of the upper headgear connector of FIG. 6-1, in overlapping relation;

FIG. 8-2 is a top view showing different sizes of the upper headgear connector of FIG. 6-1, in spaced relation;

FIG. 8-3 is a side view showing different sizes of the upper headgear connector of FIG. 6-1, in overlapping relation;

FIG. 8-4 is a side view showing different sizes of the upper headgear connector of FIG. 6-1, in spaced relation;

FIG. 8-5 is a rear view showing different sizes of the upper headgear connector of FIG. 6-1, in overlapping relation;

FIG. 8-6 is a rear view showing different sizes of the upper headgear connector of FIG. 6-1, in spaced relation;

FIG. 8-7 is a front view showing different sizes of the upper headgear connector of FIG. 6-1, in overlapping relation;

FIG. 8-8 is a front view showing different sizes of the upper headgear connector of FIG. 6-1, in spaced relation;

FIGS. 9-1 and 9-2 show exemplary dimensions for a large size mask system of FIG. 1-1;

FIGS. 9-3 and 9-4 show exemplary dimensions for a medium size mask system of FIG. 1-1;

FIGS. 9-5 and 9-6 show exemplary dimensions for a small size mask system of FIG. 1-1;

FIG. 10-1 is an enlarged front perspective view showing the frame and upper headgear connector of the mask system of FIG. 1-1;

FIG. 10-2 is an enlarged front perspective view showing the frame of the mask system of FIG. 1-1;

FIG. 10-3 is an enlarged rear perspective view showing the upper headgear connector of the mask system of FIG. 1-1;

FIG. 10-4 is an enlarged rear perspective view showing the frame and upper headgear connector of the mask system of FIG. 1-1;

FIG. 10-5 is a cross-sectional view showing the frame and upper headgear connector of the mask system of FIG. 1-1;

FIG. 10-6 is a cross-sectional view showing the frame and upper headgear connector of the mask system of FIG. 1-1;

FIG. 10-7 is a cross-sectional view showing the frame, cushion, and upper headgear connector of the mask system of FIG. 1-1;

FIG. 11-1 is a front perspective view of a mask system according to another embodiment of the present invention;

FIG. 11-2 is a side perspective view of the mask system of FIG. 11-1;

FIGS. 12-1 to 12-4 are various views of a mask system according to another embodiment of the present invention;

FIGS. 13-1 to 13-4 are various views of the frame and shroud of the mask system of FIG. 12-1;

FIGS. 14-1 to 14-4 are various views of the shroud of the mask system of FIG. 12-1;

FIG. 15-1 is a top view of the frame and shroud of the mask system of FIG. 12-1 showing flexibility of the lower headgear connectors;

FIGS. 15-2 and 15-3 are bottom and front views of the mask system of FIG. 12-1 showing flexibility of the lower headgear connectors;

FIGS. 15-4 and 15-5 are front and side views of the mask system of FIG. 12-1 showing flexibility of the lower headgear connectors in use;

FIG. 16-1 is a cross-sectional view of the frame and shroud of the mask system of FIG. 12-1; and FIG. 16-2 is an enlarged top view of the frame and shroud of the mask system of FIG. 12-1.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The term "shroud" will be taken to include components that partially or fully cover a second component within the illustrated embodiments. In an embodiment, the shroud may include the component that partially covers or is mounted on the frame components of the illustrated embodiments.

1. Mask System

As described in greater detail below, the mask system includes a frame, a cushion provided to the frame and adapted to form a seal with the patient's face, a shroud provided to the frame and adapted to attach headgear, and an elbow provided to the frame and adapted to be connected to an air delivery tube that delivers breathable gas to the patient. Headgear may be removably attached to the top and bottom of the frame either directly or via the shroud, which provides headgear connection points for headgear positioned and arranged to stably maintain the mask system in position on the patient's face. The mask system is intended for use in positive pressure therapy for users with Obstructive Sleep Apnea (OSA) or another respiratory disorder.

While each embodiment below is described as including a full-face or oro-nasal interface type, each embodiment may be adapted for use with other suitable interface types. That is, the interface type is merely exemplary, and each embodiment may be adapted to include other interface types, e.g., nasal interface, nasal mask, nozzles, nasal prongs, etc.

Also, each illustrated embodiment includes features that may be used with the embodiments and/or components described in PCT Application No. PCT/AU2009/000241, filed Feb. 27, 2009, as would be apparent to those of ordinary skill in the art. The above noted application is incorporated herein by reference in its entirety. However, it should be appreciated that any single feature or combination of features in any of the embodiments may be applied to other suitable mask arrangements.

1.1 Frame

Figure 1:
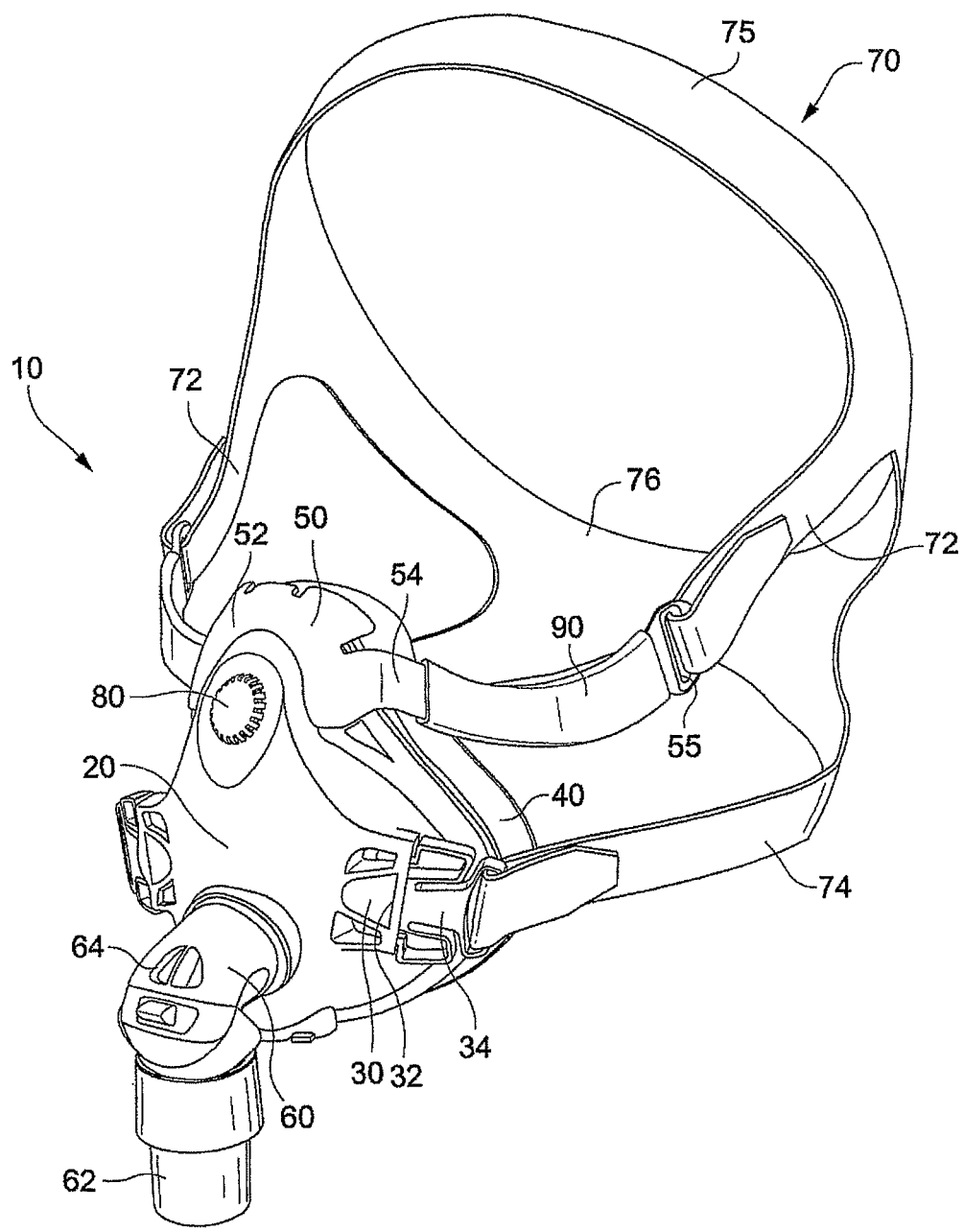
FIG. 1-1 is a perspective view of a mask system according to an embodiment of the present invention.
Figures 1, 4:
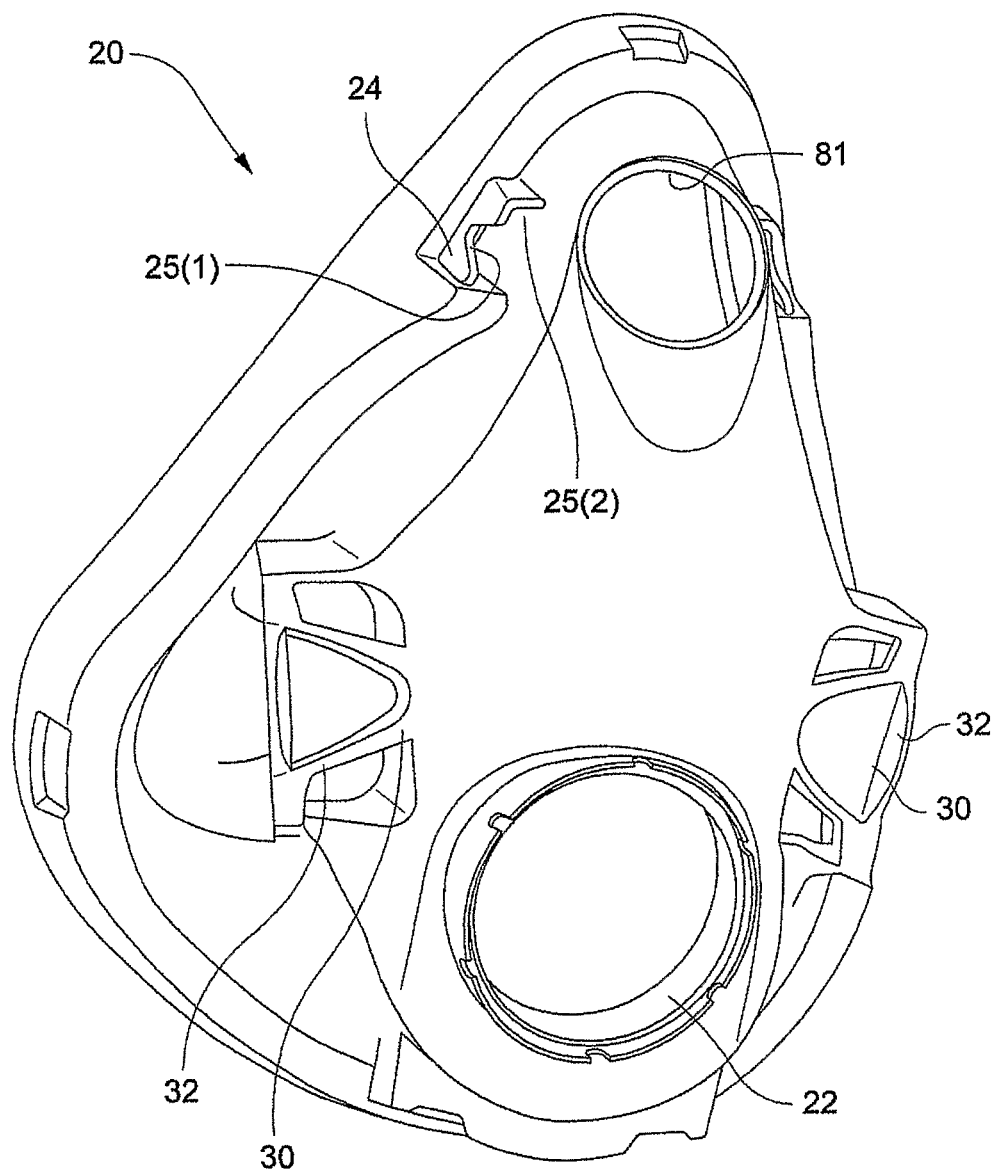
Figures 2, 4:
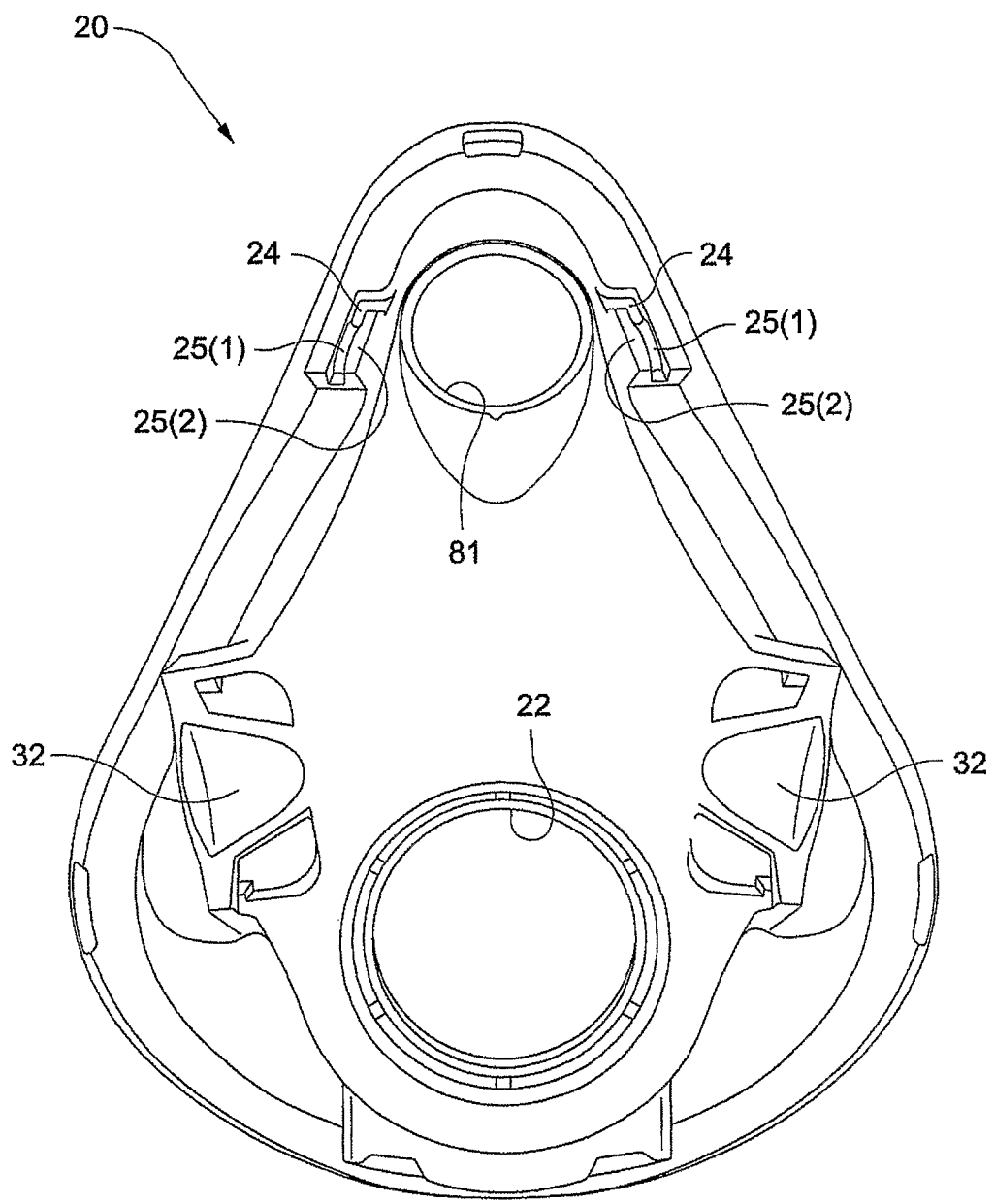
Figures 3, 4:
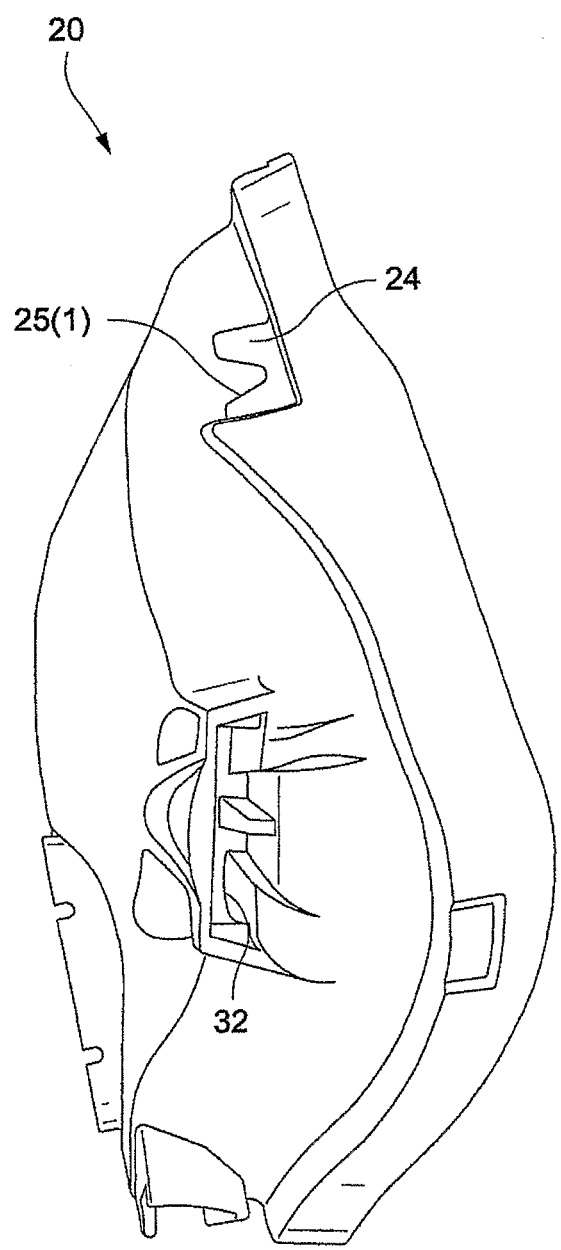
Figure 4:
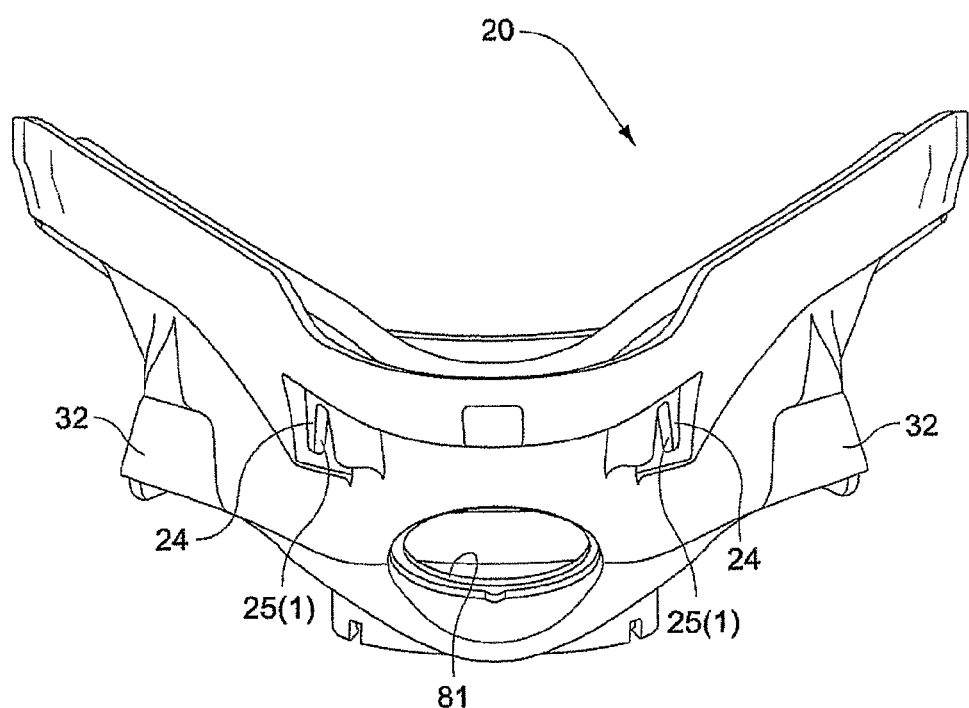

As shown in FIGS. 1-1 to 4-4, the frame 20 of the mask system 10 is structured to maintain the cushion 40, shroud 50, and elbow 60 in an operative position with respect to the patient's face.

The frame 20 defines a breathing chamber or cavity adapted to receive the patient's nose and mouth and provide air communication to the patient. One or lower portion of the frame includes an opening 22 adapted to receive or otherwise communicate with the elbow 60 (e.g., swivel elbow) and another or upper portion of the frame includes an opening 81 to support a vent arrangement 80 (e.g., see FIGS. 1-1 to 2-2) for gas washout. In an embodiment, the vent arrangement 80 may be integrally formed in one piece with the frame. Also, the upper portion of the frame includes an interfacing structure adapted to interface or otherwise removably connect to the shroud 50, as described in greater detail below.

In an alternative embodiment, the lower portion of the frame may also include an interfacing structure adapted to interface or otherwise removably connect to the shroud (e.g., see FIG. 16-1 described below).

1.1.1 Lower Headgear Connectors

In the embodiment of FIGS. 1-1 to 4-4, the bottom or lower portion of the frame 20 includes lower headgear connectors 30 adapted to attach headgear. The lower headgear connectors 30 may be integrally formed in one-piece with the frame. Each lower headgear connector 30 includes a clip receptacle 32 adapted to be removably interlocked with a headgear clip 34 associated with a respective headgear strap. The clips allow for easier positioning or donning/removal of the mask system.

In an embodiment, the headgear clip receptacle and clip may be similar to that on ResMed's Mirage Quattro™ mask or ResMed's Mirage Liberty™ mask. Exemplary clip arrangements are disclosed in U.S. Patent Publication Nos. 2007/0157353 and 2006/0283461, each of which is incorporated herein by reference in its entirety.

Figures 1, 2:
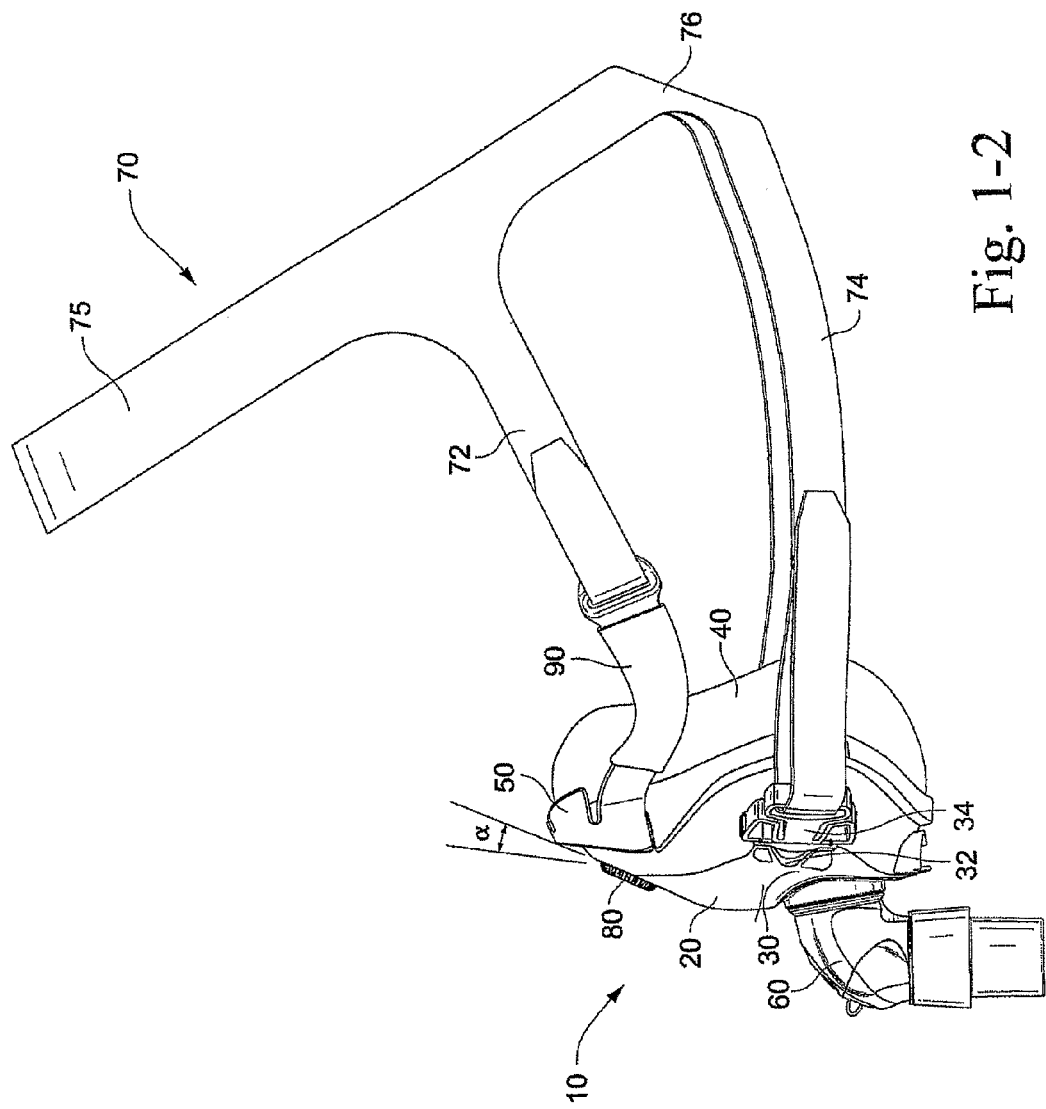
Figures 1, 2:
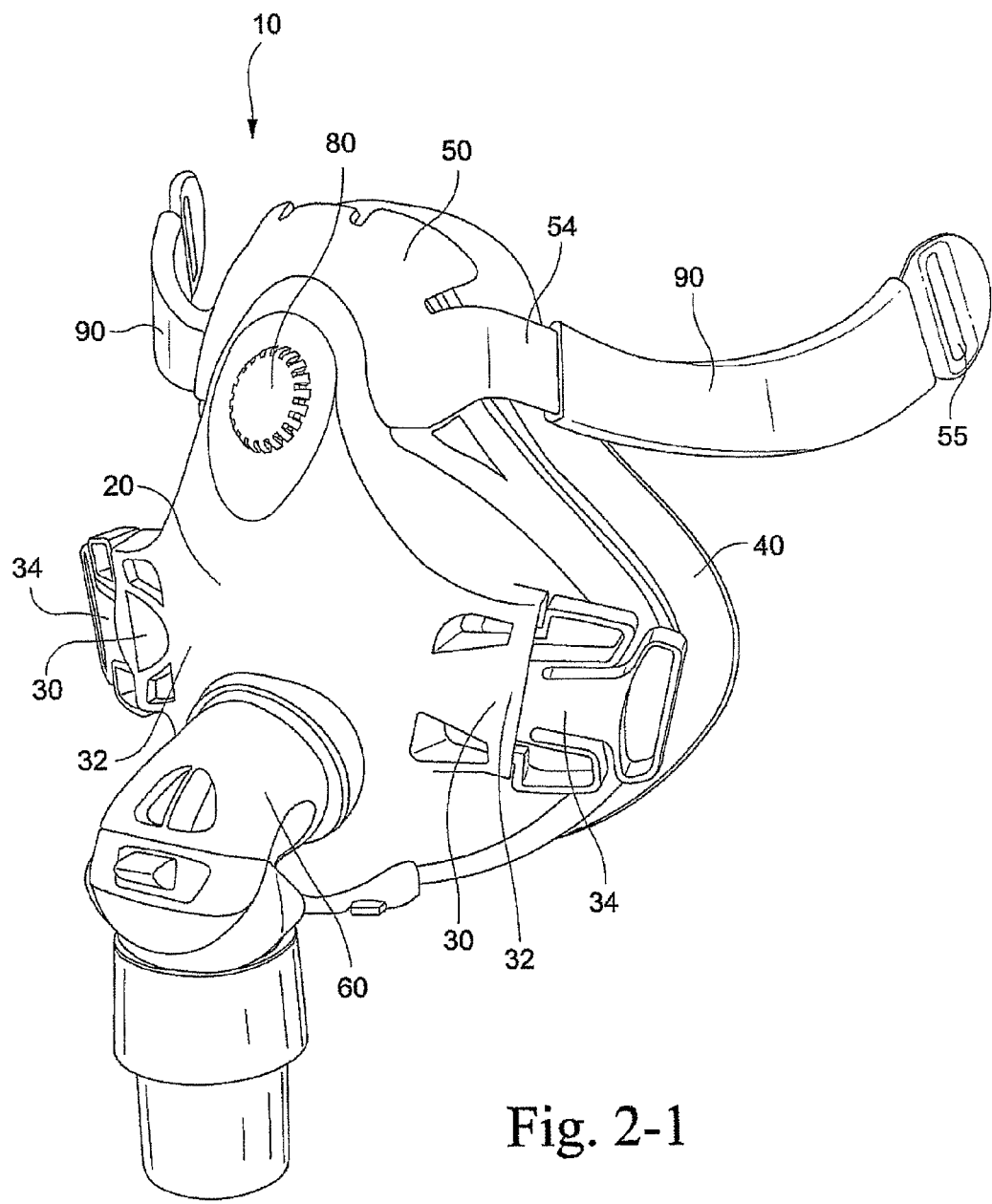
Figure 2:
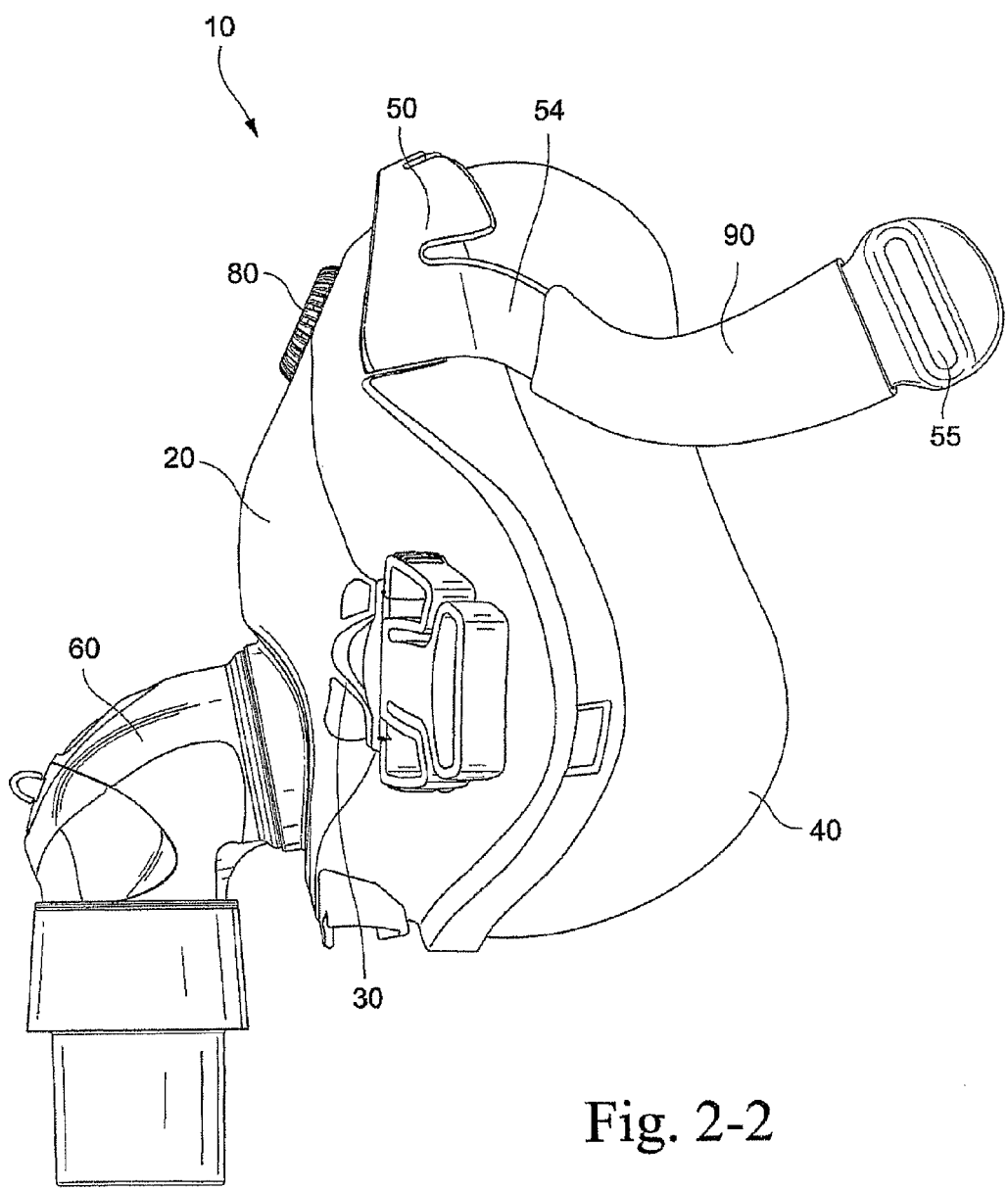
Figures 1, 5:
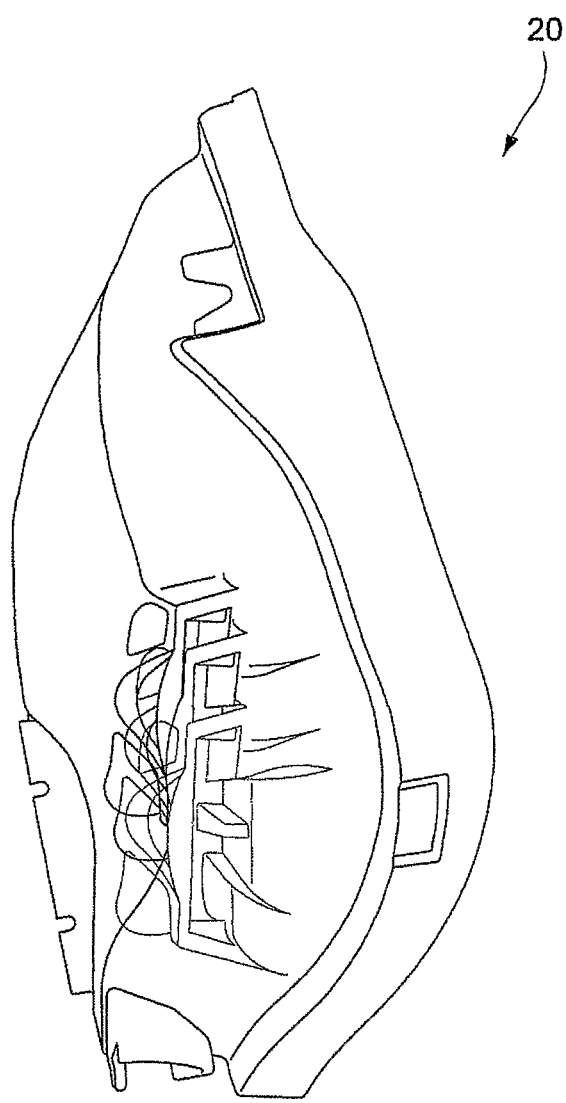
Figures 2, 5:
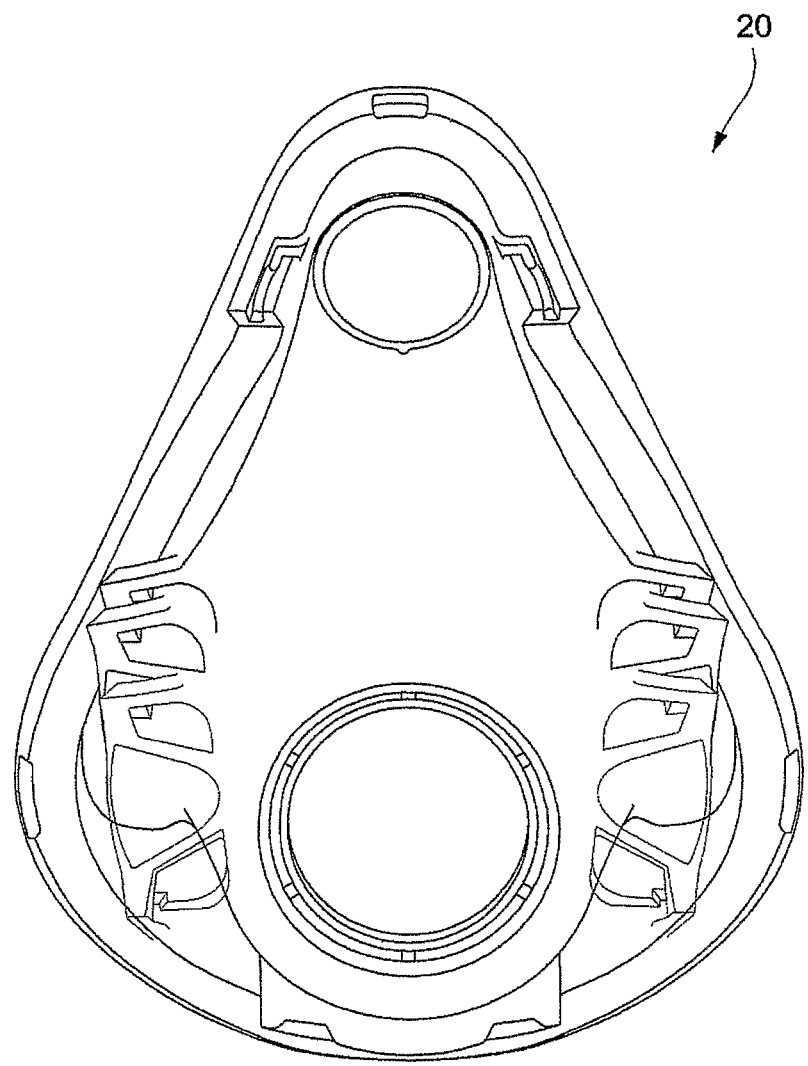

The frame may be provided in different sizes, e.g., small, medium, and large. As shown in FIGS. 5-1 and 5-2, the position of the clip receptacles 32 may change or vary between sizes, e.g., shift vertically. The positioning of the receptacles may be selected to enhance sealing, e.g., by changing the application point for headgear tension.

1.1.2 Vent Arrangement

As best shown in FIGS. 1-1 to 2-2, 10-1, 10-2, and 10-4, the vent arrangement 80 is in the form of a diffused vent cap that may be integrally formed in one-piece with the frame 20. The vent cap includes a base wall 82, a dome 84 that extends upwardly from the base wall 82 above the horizontal surface of the base wall 82, and multiple vent holes 86 arranged on an annular side wall of the dome 84 to provide diffuse airflow that is directed away from the patient's face as well as the bed partner (e.g., see FIGS. 10-1 and 10-4). The angle of the diffused airflow can be tuned by altering the dimensions of the vent cap. The diffused airflow provides venting over a larger area to minimize jetting and may also reduce noise.

In the illustrated embodiment, as shown in FIG. 1-2, the vent cap 80 directs exhaust flow up and out from the mask, e.g., angle a is about 0-30°, e.g., 15°, 20°. In an embodiment, angle a is about 20° to ensure that air is not directed onto the patient's face.

In the illustrated embodiment, the vent holes 86 are arranged radially along the annular side wall of the dome 84 to radially divide the exhaust flow in 360°. In an embodiment, the vent cap may include 10-40 vent holes, e.g., 25 vent holes.

In the illustrated embodiment, the diameter of the vent cap (when viewed from above) is about 10-25 mm, e.g., 18 mm.

Further details and/or alternative arrangements of such vent arrangement are disclosed in U.S. Patent Application Publication No. US 2009/0050156 A1, which is incorporated herein by reference in its entirety.

However, it should be appreciated that the vent arrangement may include other suitable arrangements, e.g., different number of holes, hole arrangement, positioning on frame, etc. Also, it should be appreciated that the vent arrangement may be in the form of a vent insert (e.g., elastomeric vent insert) that is adapted to be removably supported within an outlet opening in the frame. In addition, it should be appreciated that the vent arrangement may be provided to the elbow.

1.2 Shroud

The shroud is connected to the frame and is structured to attach headgear to the mask system. The shroud may be constructed (e.g., injection molded) of resilient material including, but not limited to, plastics (such as Nylon or Nylon 12) or non-plastics. The shroud may be constructed of any suitable material which could also include: textiles, polycarbonate, polypropylene, thermoplastic elastomer (TPE), or Pocan®, etc.

1.2.1 Upper Headgear Connector or Rigidizer

Figures 1, 3:
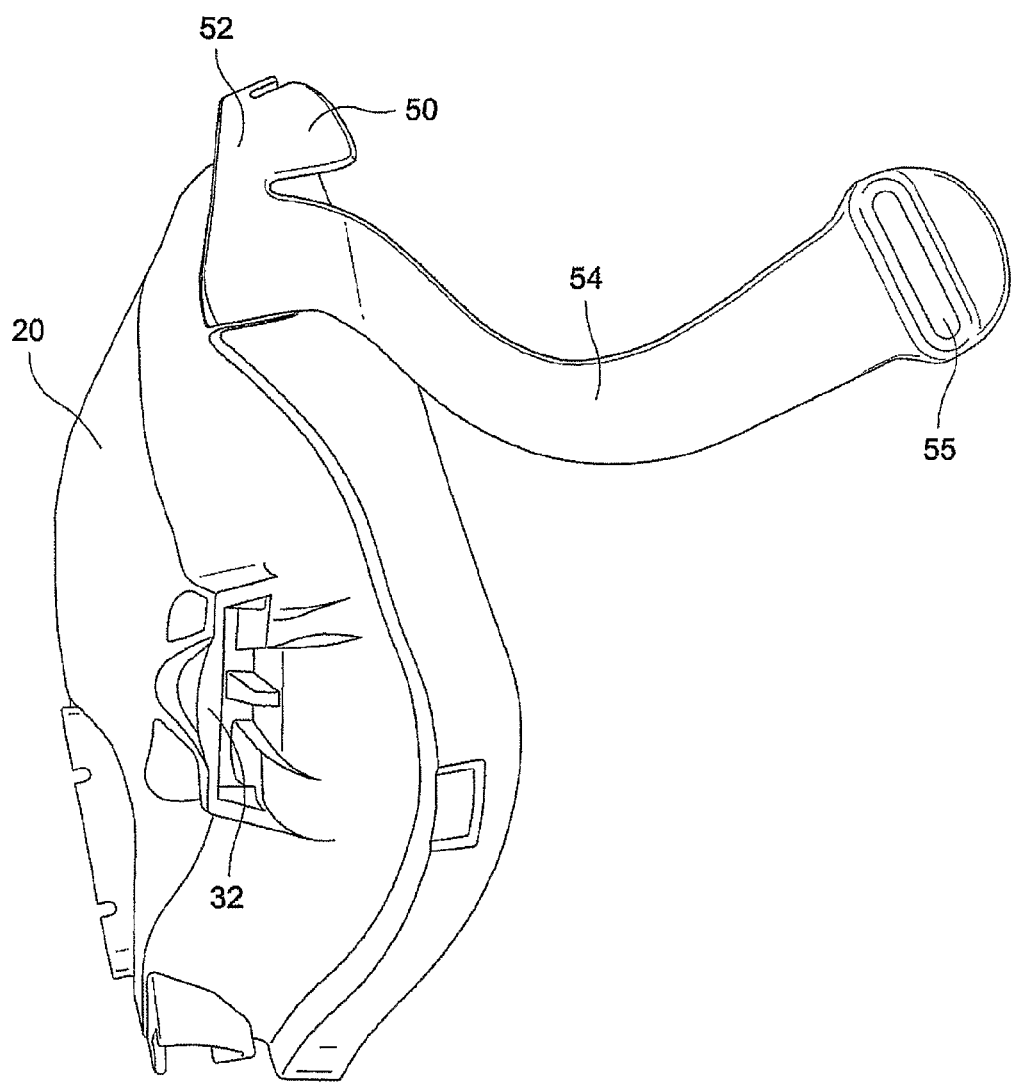
Figures 2, 3:
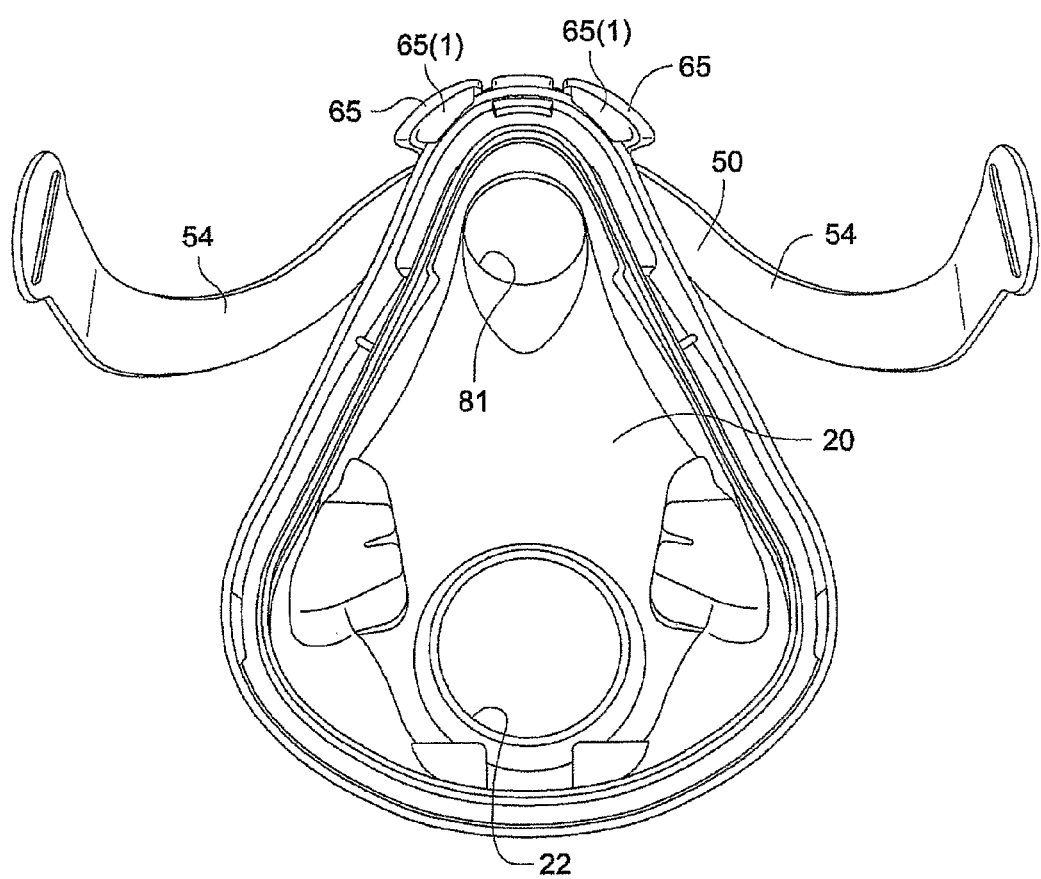

In the embodiment of FIGS. 1-1 to 3-2, the shroud 50 is in the form of a snap-on upper headgear connector or upper headgear rigidizer that is connected to the top of the frame 20 and is structured to attach upper headgear straps to the frame. This shroud is used in conjunction with the frame 20 including lower headgear connectors 30 adapted to attach lower headgear straps to the frame.

Figures 1, 6:
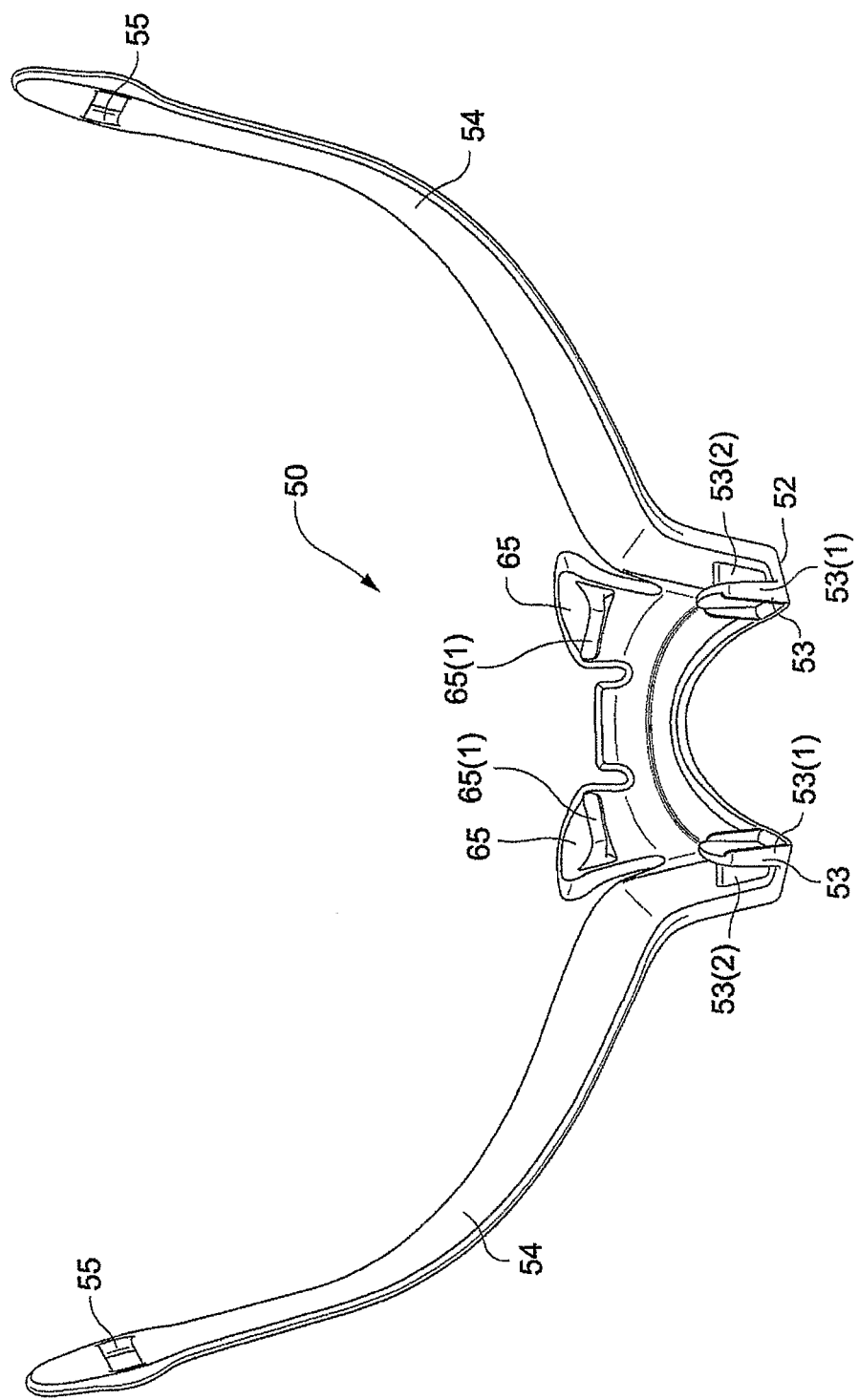
Figures 2, 6:
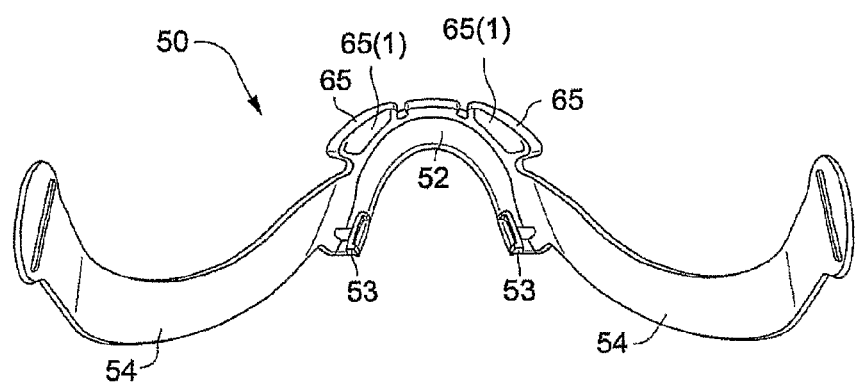
Figures 3, 6:
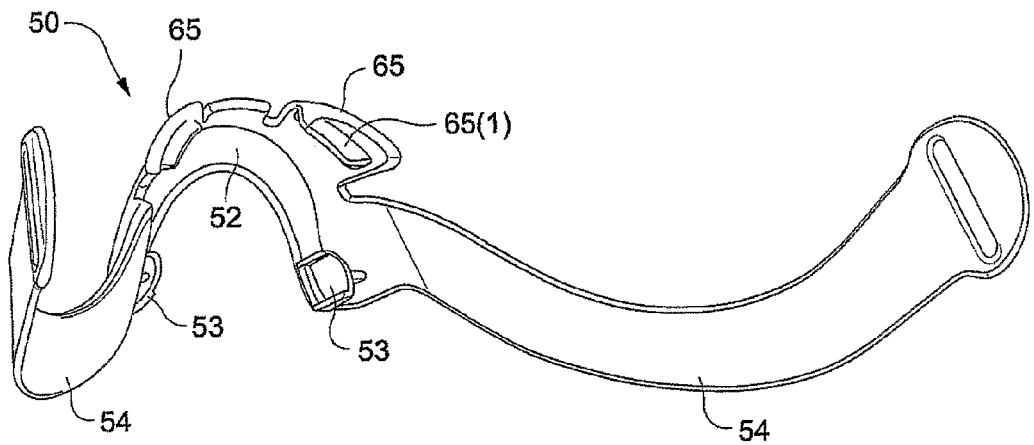
Figures 4, 6:
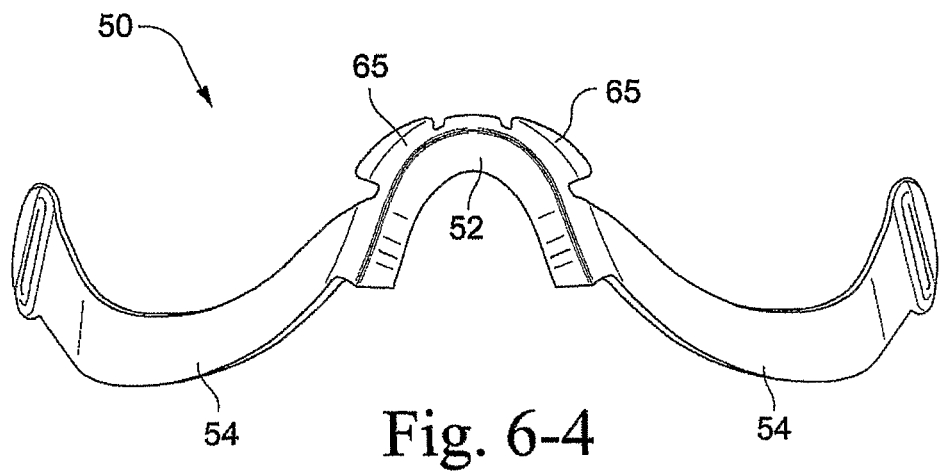
Figures 5, 6:
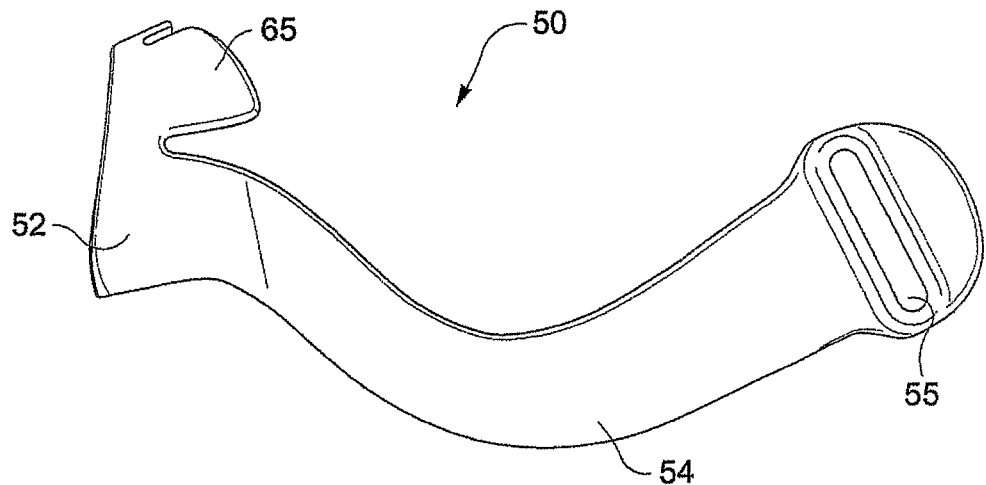
Figure 6:
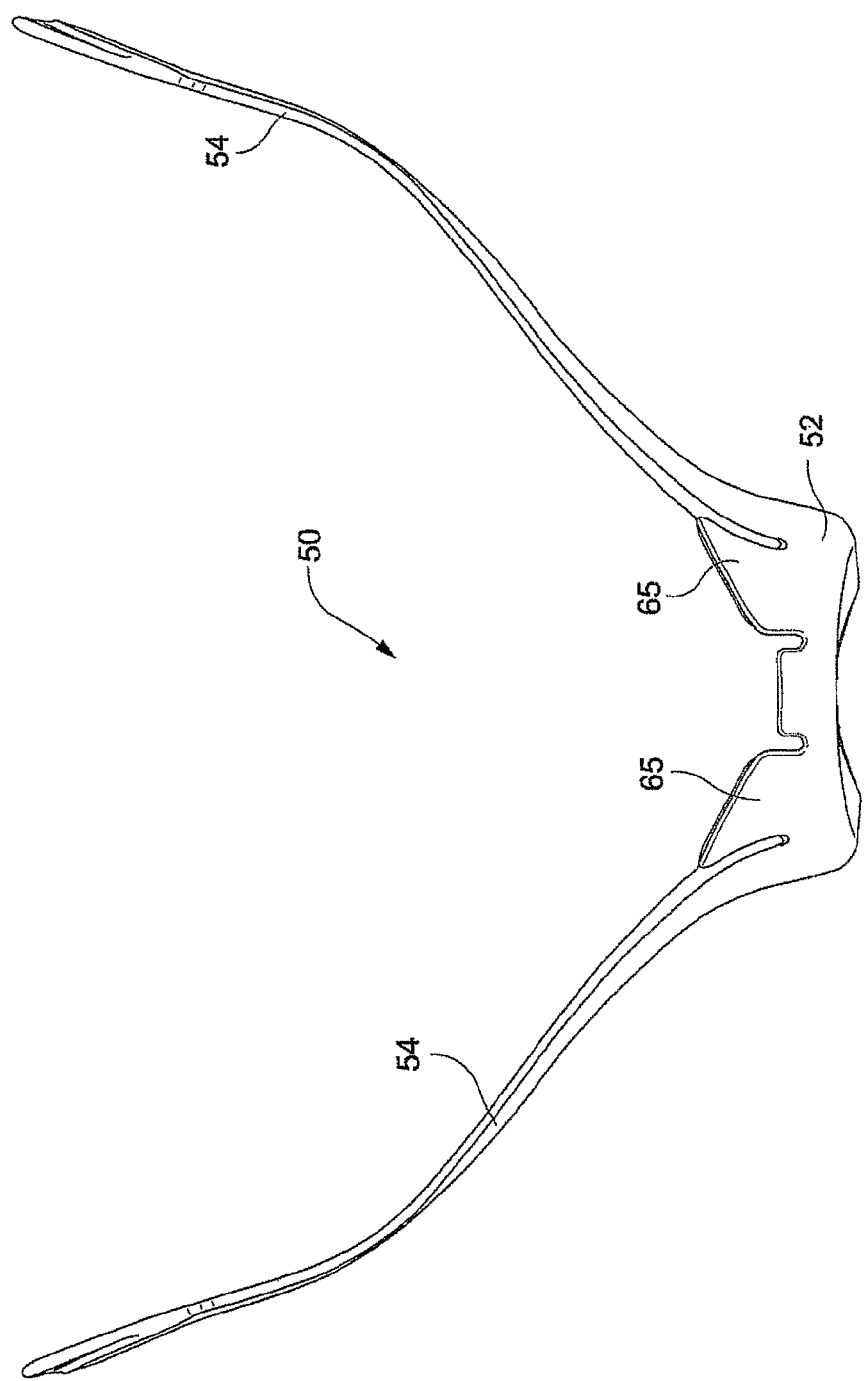

As best shown in FIGS. 6-1 to 6-6, the upper headgear rigidizer 50 includes a frame connecting portion 52 adapted to connect the upper headgear rigidizer to the frame. The frame connecting portion 52 is adapted to connect to the frame at a position proximal to the nasal bridge region or nose of the patient. The frame connecting portion 52 includes a contoured or general "U" shape to accommodate the vent arrangement 80 provided to the frame 20. Further details of connection are described below.

The upper headgear rigidizer 50 also includes arms 54 that extend from respective sides of the frame connecting portion 52. Each arm 54 includes a slot or receiving hole 55 at the free end thereof adapted to receive a respective headgear strap. In use, the arms 54 extend around the face of the patient in a generally concave angle below the eyes of the patient so as to avoid the patient's field of view, i.e., direct headgear away from the patient's eyes. The hole 55 may alternately be replaced with a series or plurality of holes to provide for increased adjustability.

Figures 1, 11:
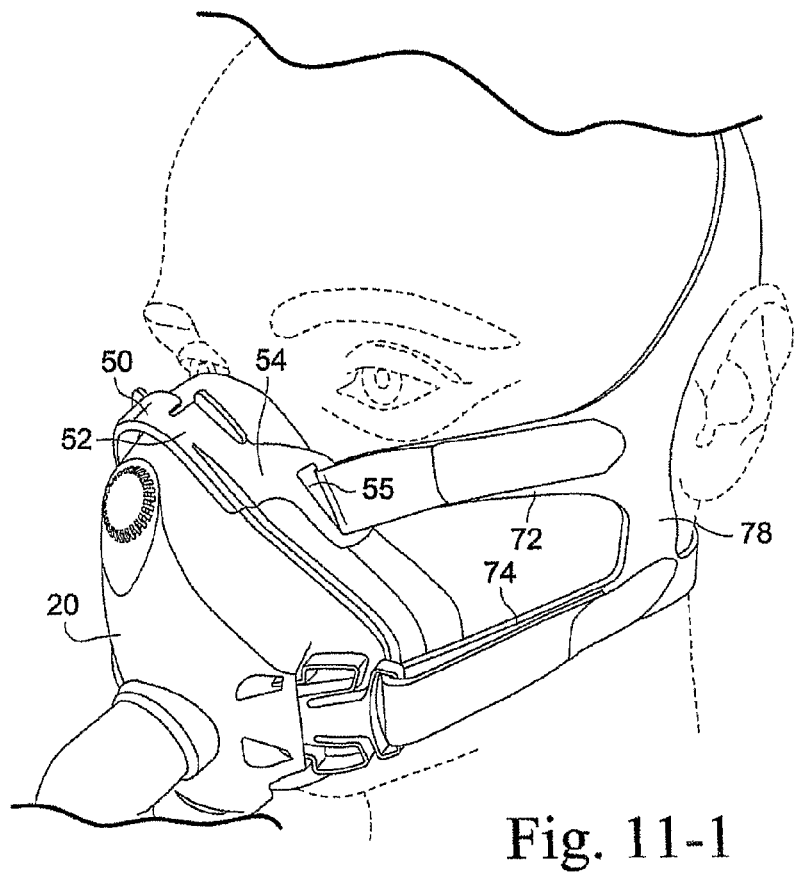
Figures 2, 11:
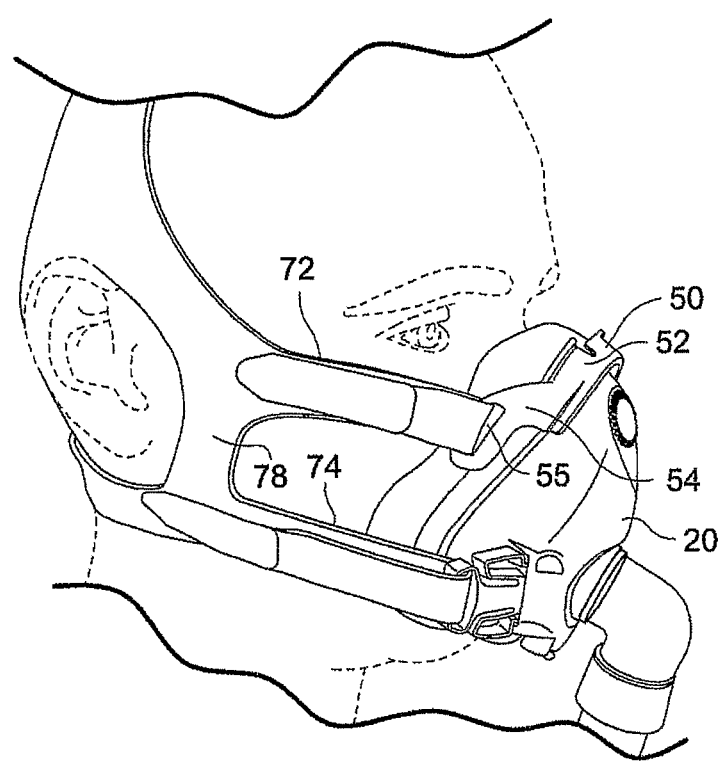

FIGS. 11-1 and 11-2 illustrate an upper headgear rigidizer 50 according to an alternative embodiment. In this embodiment, the arm 54 is abbreviated or relatively short.

Preferably, the rigidizers may function to modify the force vectors acting on the mask system. In these embodiments, the rigidizer provides an attachment point for the headgear at the upper most extreme of the mask system, while simultaneously providing a means to avoid the headgear straps from entering or impeding the patient's field of vision. The rigid connection between the rigidizer and the top of the mask system allows adjustments to the headgear to be transmitted to the top of mask system via the rigidizer. Additionally, the rigidizer may act as a type of lever to provide a mechanical advantage to any turning force applied to them.

1.2.2 Different Sizes

Figures 1, 8:
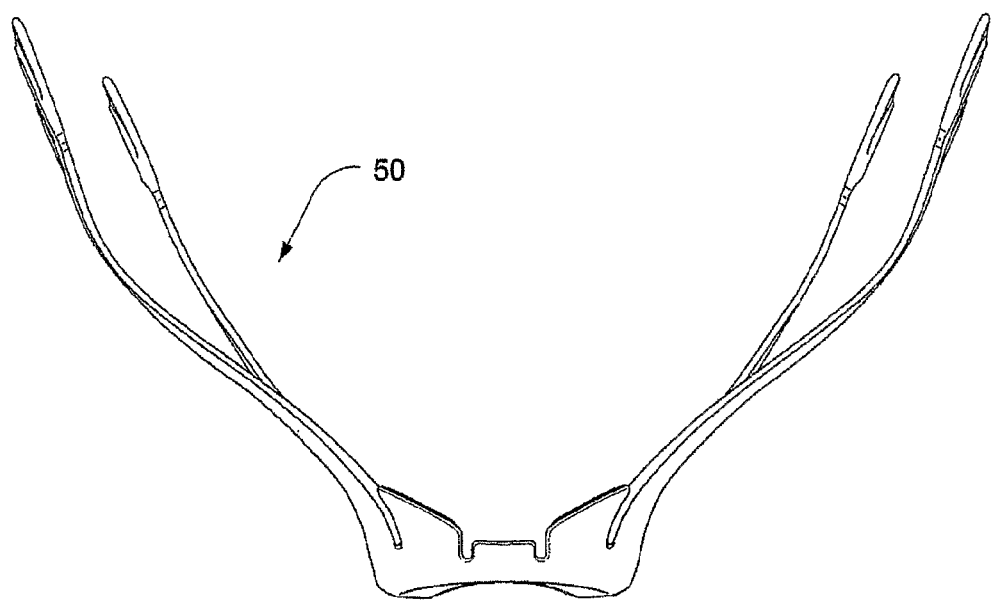
Figures 2, 8:
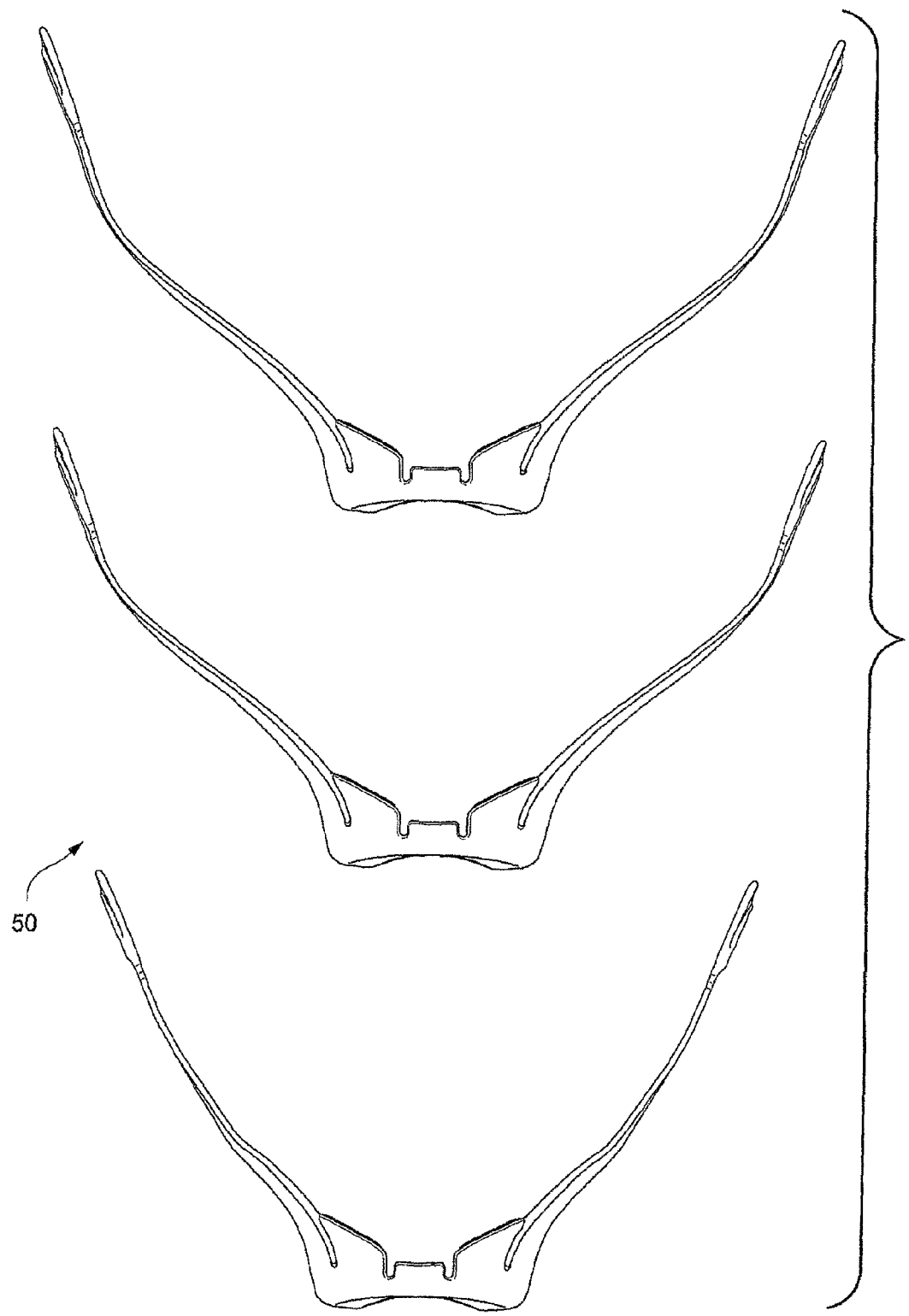
Figures 3, 8:
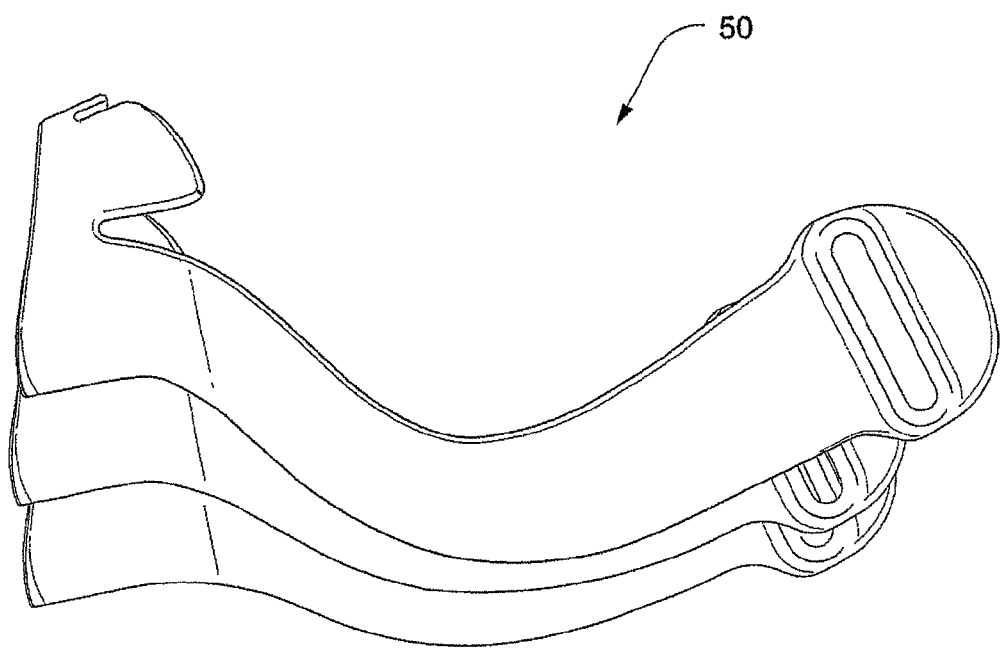
Figures 4, 8:
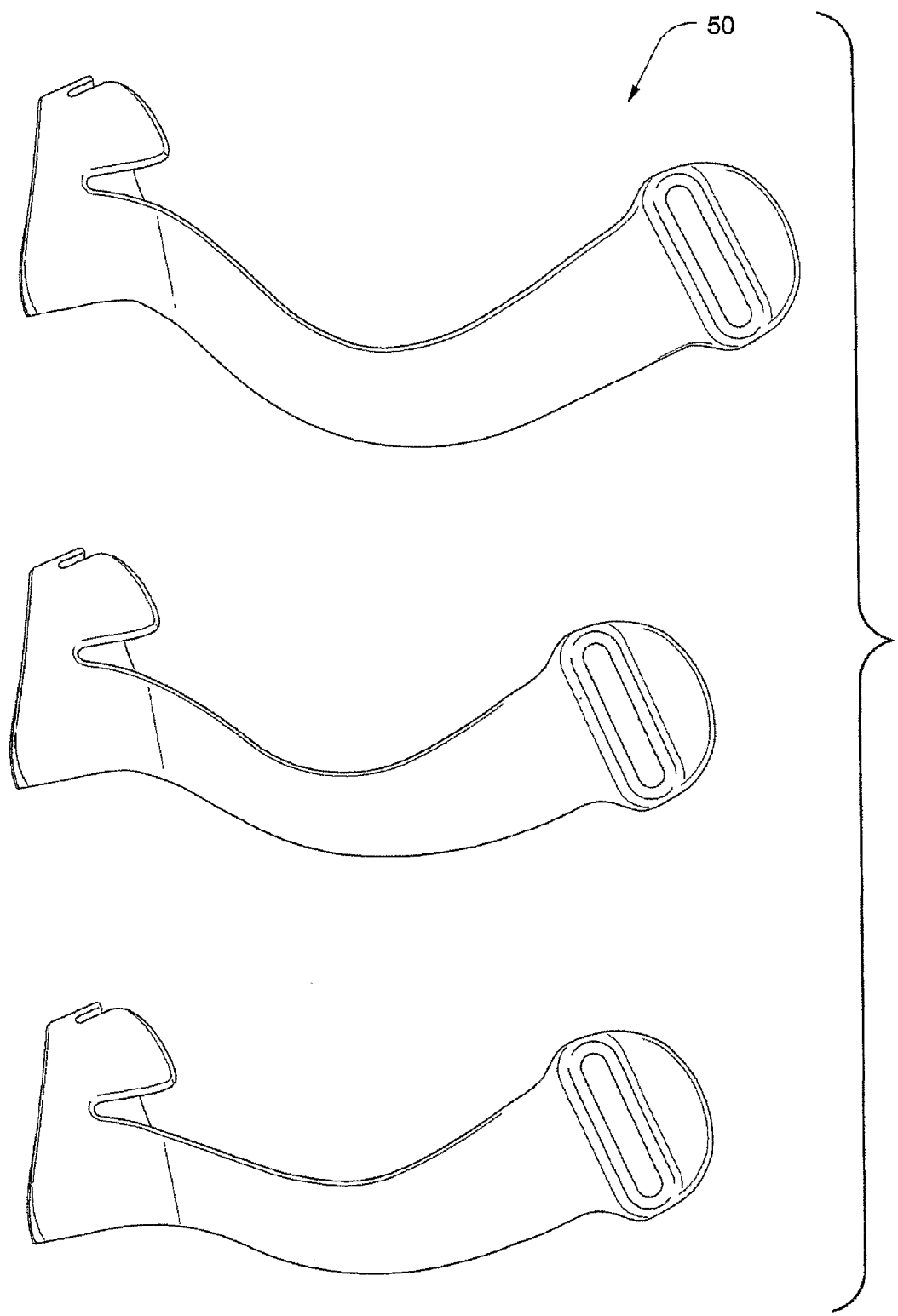
Figures 5, 8:
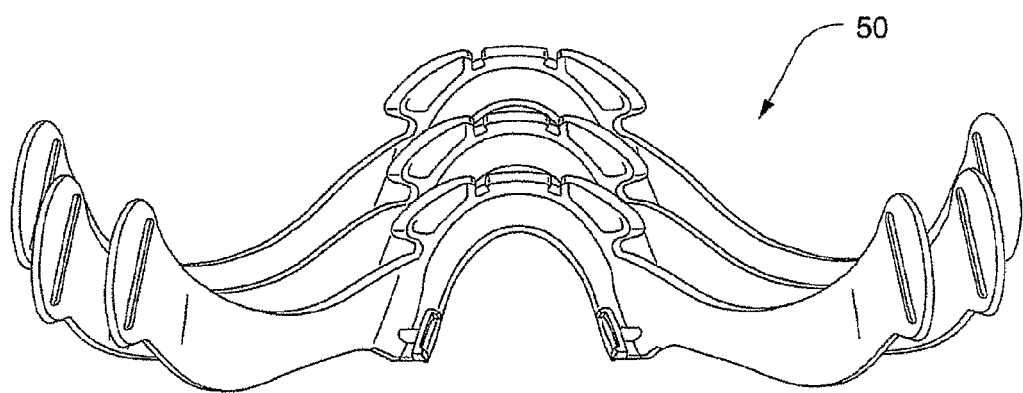
Figures 6, 8:
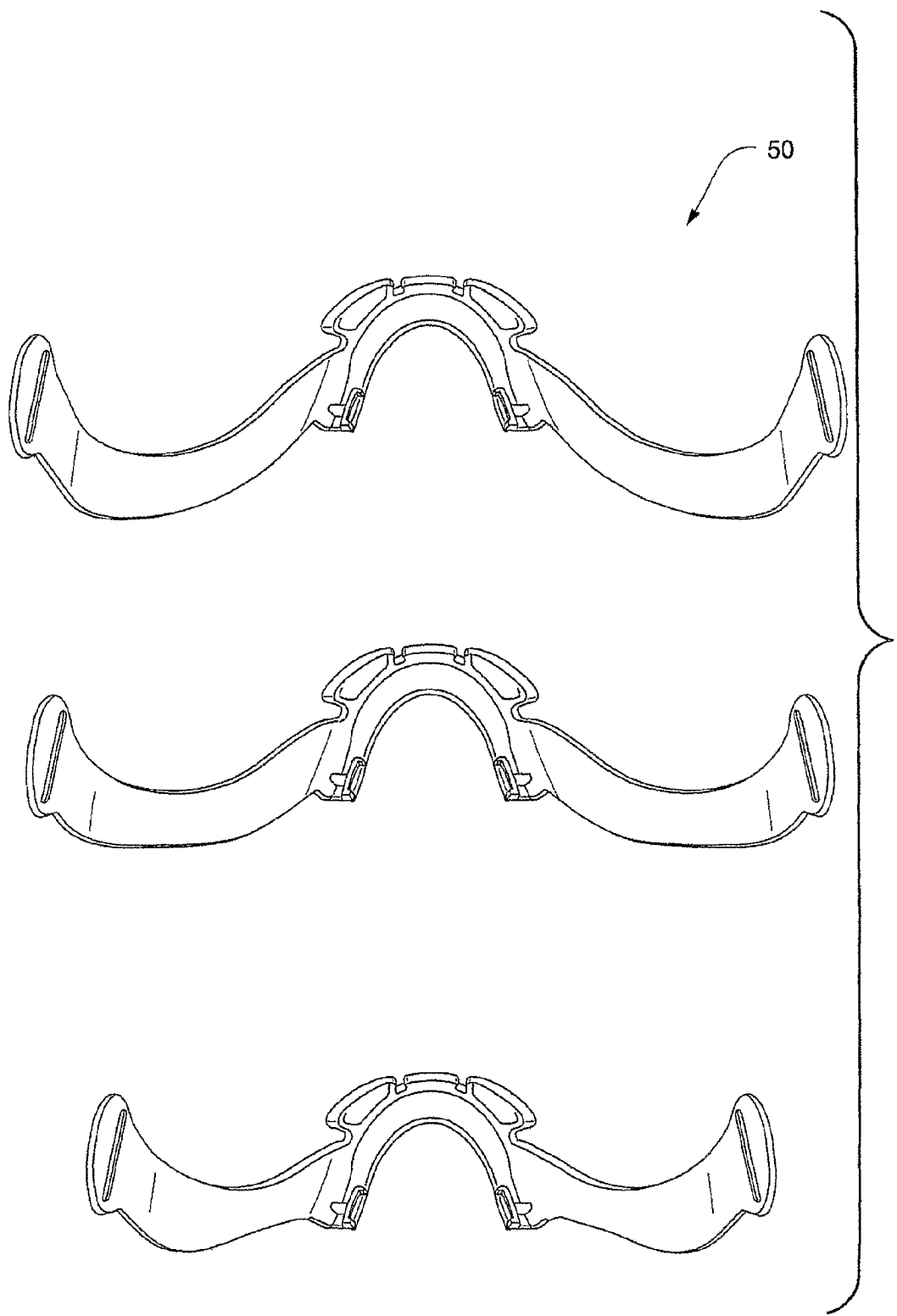
Figures 7, 8:
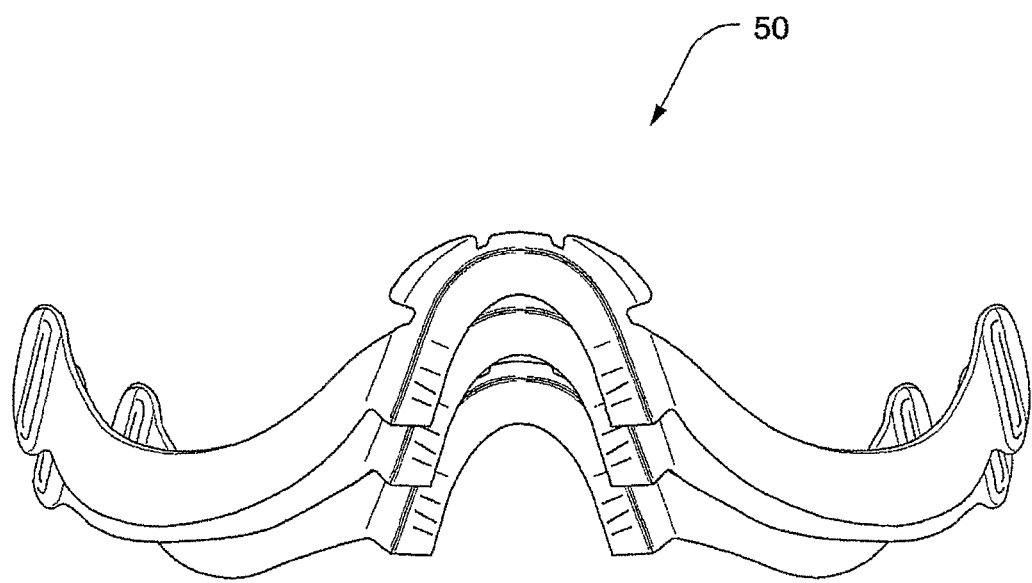
Figure 8:
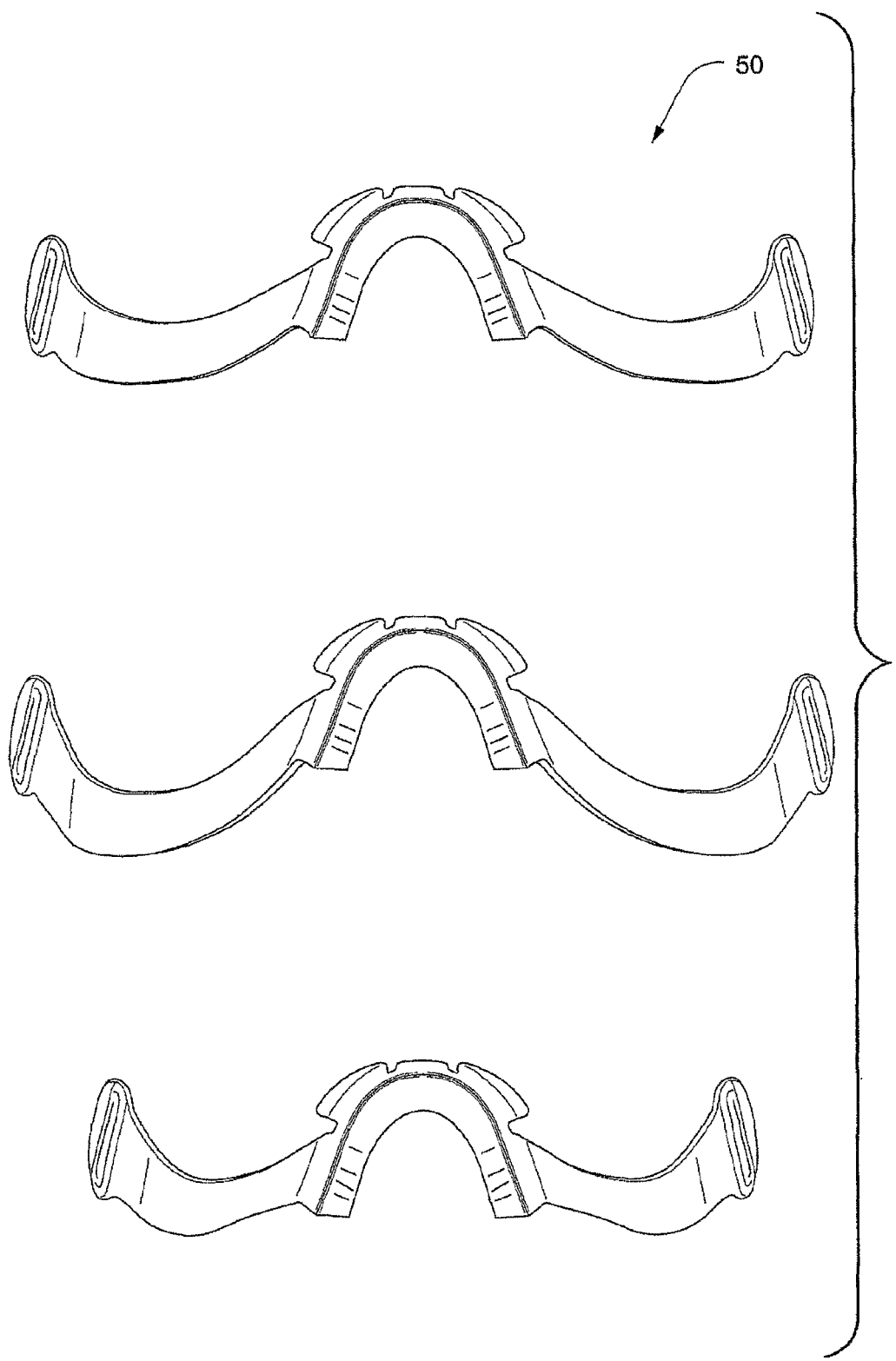

The upper headgear rigidizer 50 may be provided in different sizes, e.g., small, medium, and large, e.g., for use with different size frames as described above or a one size fits all type of frame. For example, as shown in FIGS. 8-1 to 8-8, the size, angle, and/or orientation of the arms may vary or change between sizes.

Figures 1, 9:
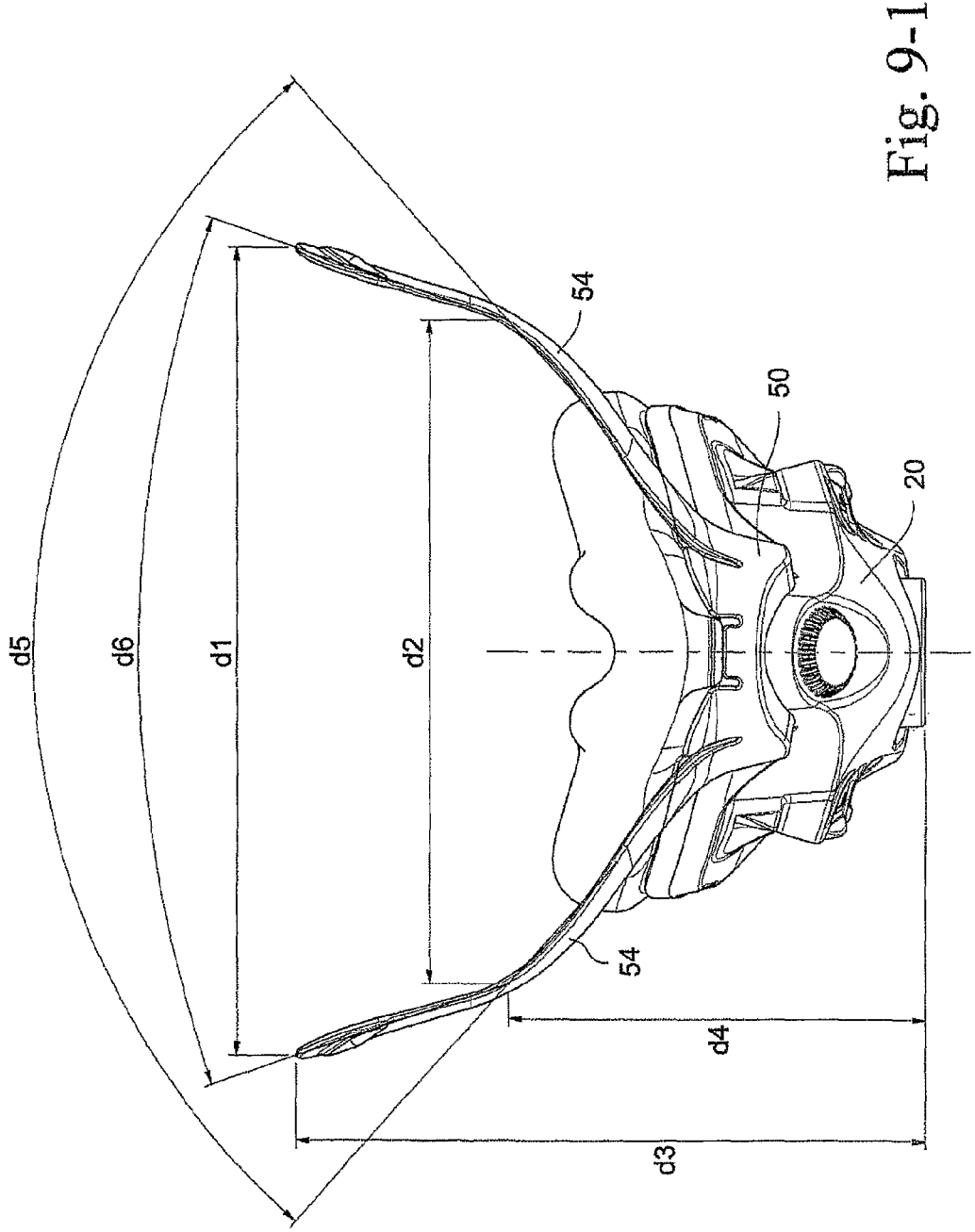
Figures 2, 9:
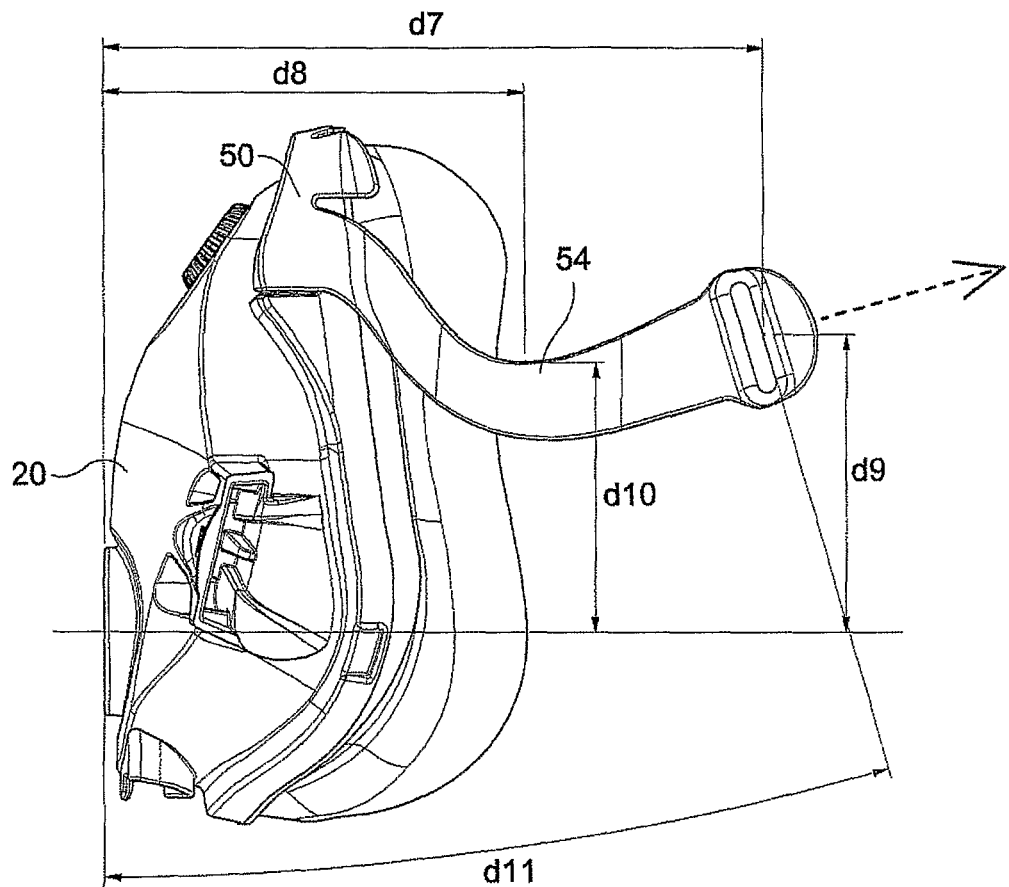
Figures 3, 9:
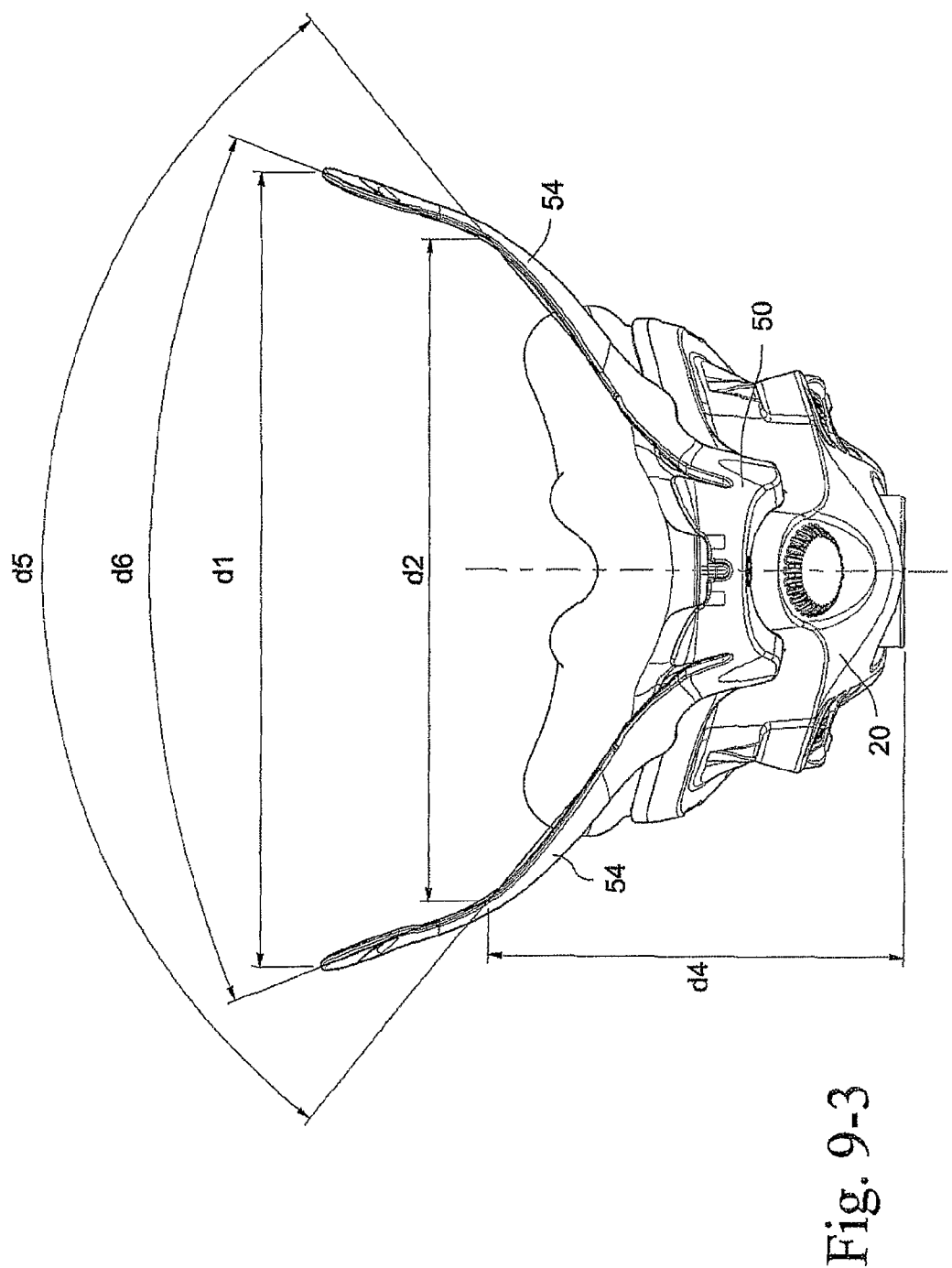
Figures 4, 9:
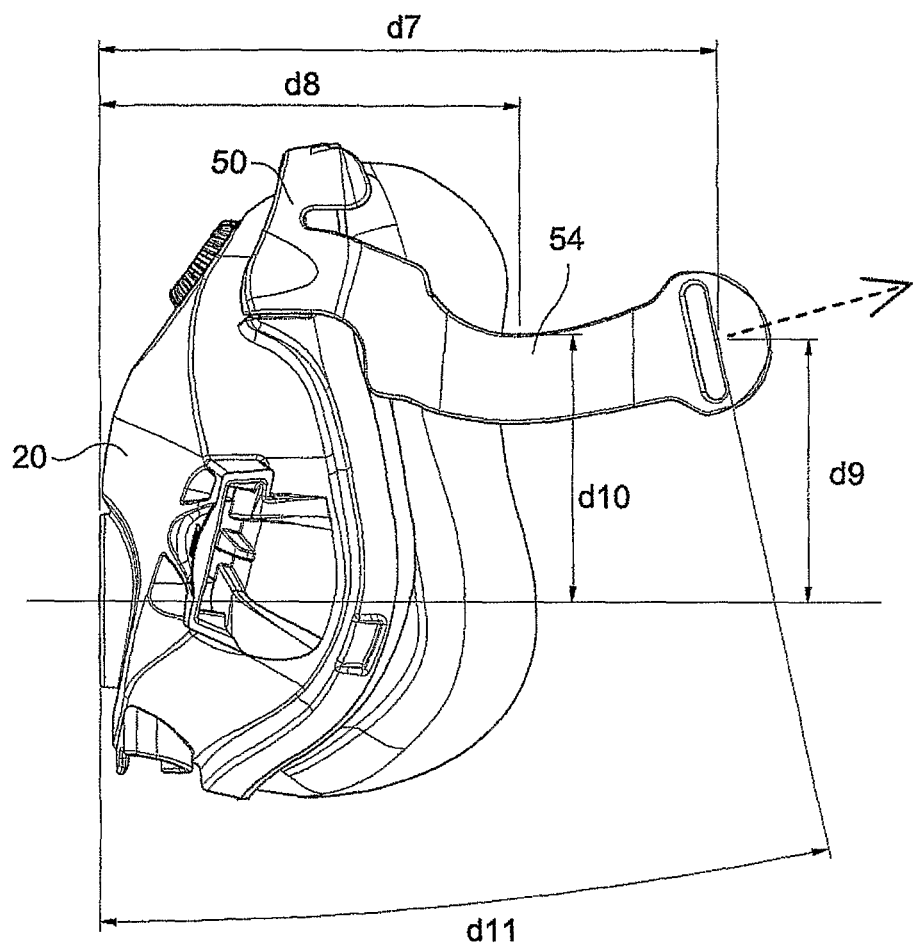
Figures 5, 9:
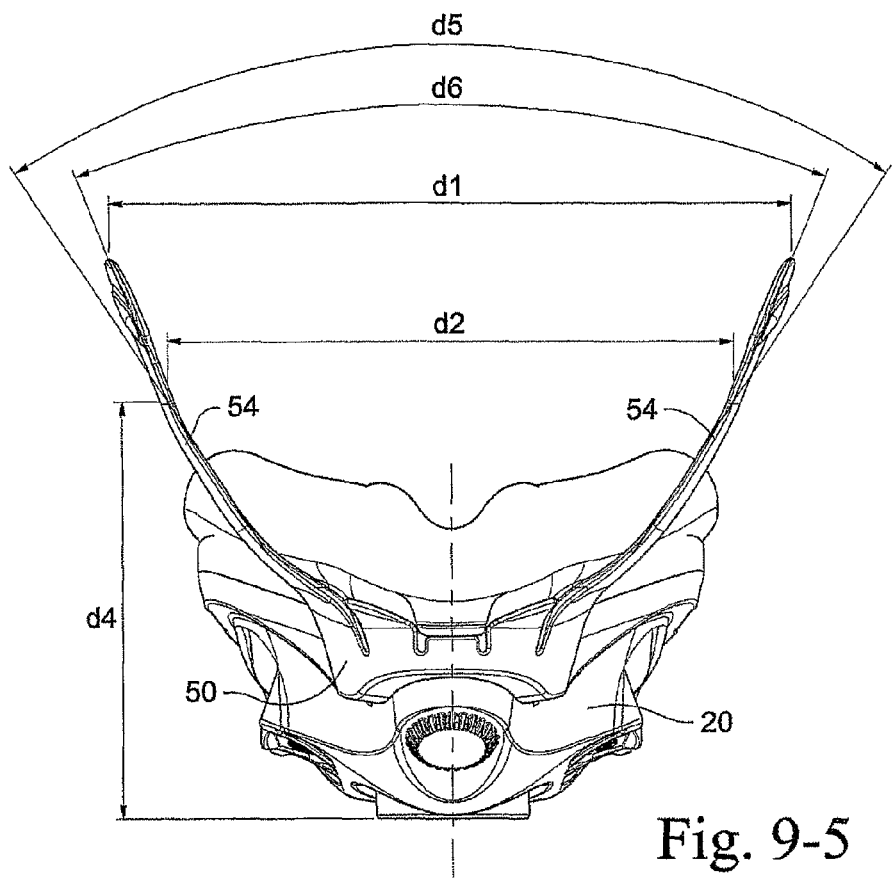
Figures 6, 9:
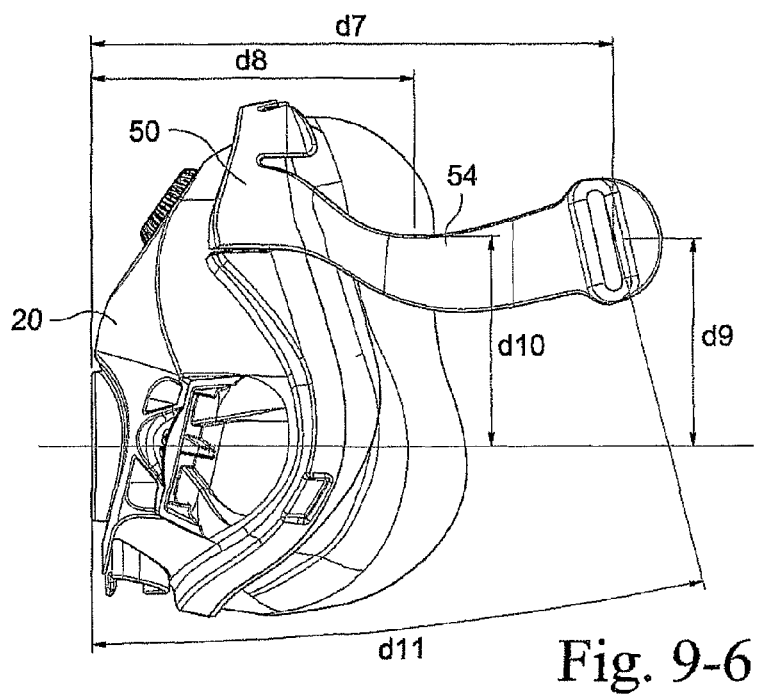

As shown in FIGS. 9-1 and 9-2, a large size upper headgear rigidizer may include the following dimensions: d1 of about 120-180 mm (e.g., 153 mm), d2 of about 116-136 mm (e.g., 126 mm), d3 of about 107-127 mm (e.g., 117 mm), d4 of about 68-88 mm (e.g., 78 mm), d5 of about 88-108° (e.g.,) 98°, d6 of about 28-48° (e.g.,) 38°, d7 of about 98-118 mm (e.g., 108 mm), d8 of about 59-79 mm (e.g., 69 mm), d9 of about 39-59 mm (e.g., 49 mm), d10 of about 35-55 mm (e.g., 45 mm), and d11 of about 6-26° (e.g.,) 16°.

As shown in FIGS. 9-3 and 9-4, a medium size upper headgear rigidizer may include the following dimensions: d1 of about 120-163 mm (e.g., 148 mm), d2 of about 113-133 mm (e.g., 123 mm), d4 of about 66-86 mm (e.g., 76 mm), d5 of about 92-112° (e.g.,) 102°, d6 of about 34-54° (e.g.,) 44°, d7 of about 88-108 mm (e.g., 98 mm), d8 of about 57-77 mm (e.g., 67 mm), d9 of about 33-53 mm (e.g., 43 mm), d10 of about 33-53 mm (e.g., 43 mm), and d11 of about 2-22° (e.g.,) 12°.

As shown in FIGS. 9-5 and 9-6, a small size upper headgear rigidizer may include the following dimensions: d1 of about 115-160 mm (e.g., 126 mm), d2 of about 94-114 mm (e.g., 104 mm), d4 of about 68-88 mm (e.g., 78 mm), d5 of about 56-76° (e.g.,) 66°, d6 of about 34-54° (e.g.,) 44°, d7 of about 86-106 mm (e.g., 96 mm), d8 of about 49-69 mm (e.g., 59 mm), d9 of about 29-49 mm (e.g., 39 mm), d10 of about 29-49 mm (e.g., 39 mm), and d11 of about 2-22° (e.g.,) 12°.

It is noted that dimension d1 for the different sizes is a width of the arms and relates to fit across face widths. It is noted that dimension d7 for the different sizes relates to fit and clearance between the patient's eyes/ears. It is noted that dimension d11 for the different sizes relates to the headgear force vector (indicated as a dashed arrow in FIGS. 9-2, 9-4, and 9-6). In an embodiment, the arms may be contoured or flexed such that the arms lay substantially flat or horizontal (when viewed from the top such as FIG. 9-1), e.g., to accommodate largest face range.

1.2.3 Upper and Lower Headgear Connectors

FIGS. 12-1 to 16-2 illustrate a mask system 210 including a shroud 250 with both upper and lower headgear connectors 251, 231. The shroud 250 is used in conjunction with the frame 220 including no integral headgear connectors.

Figures 1, 15:
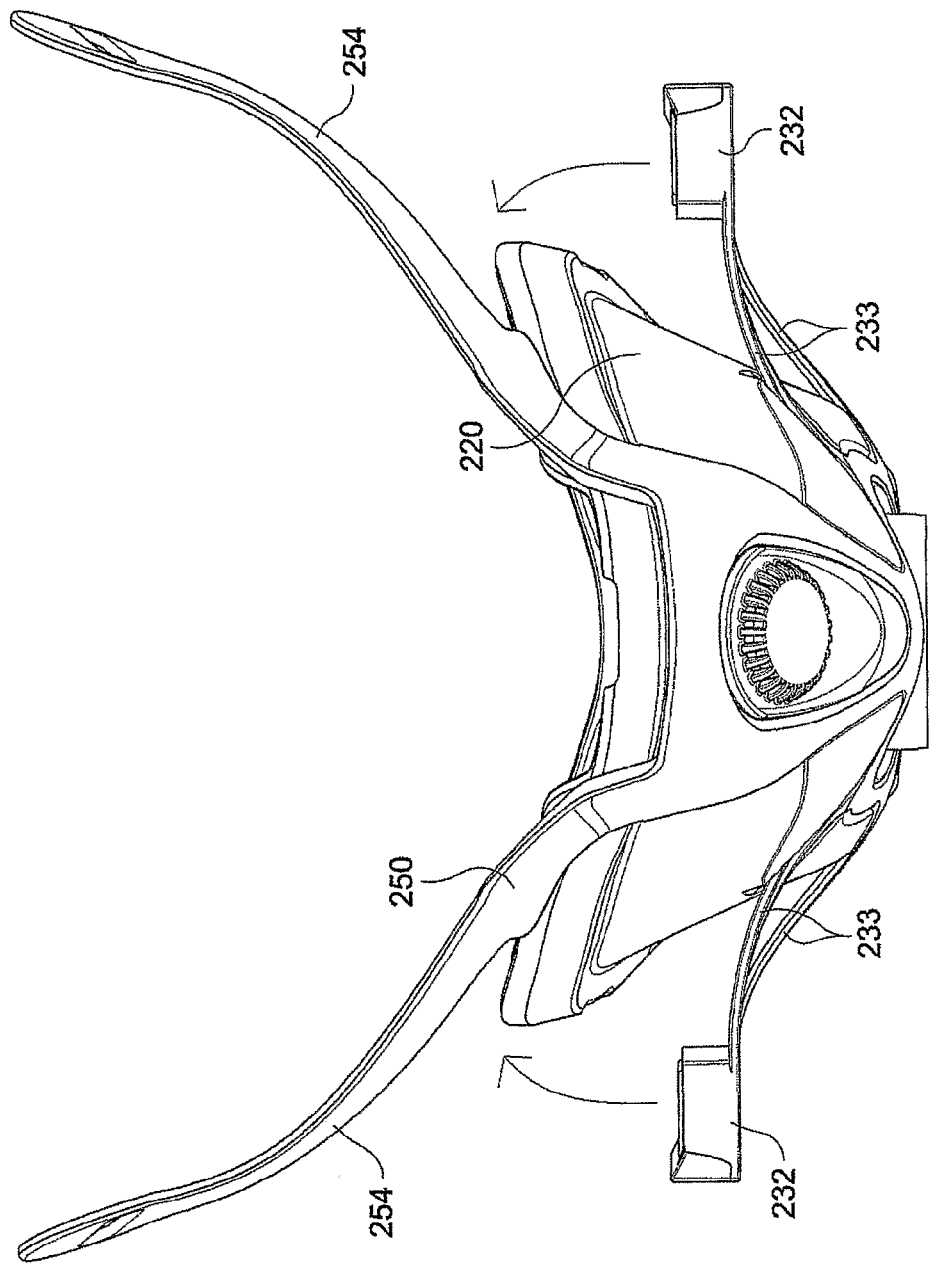
Figures 2, 15:
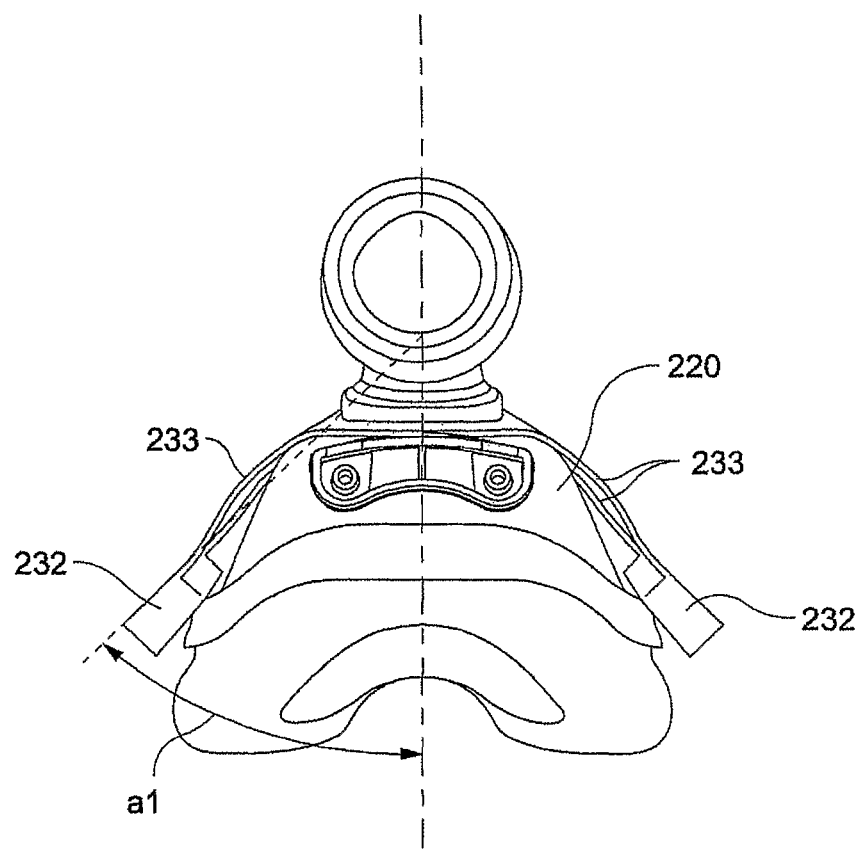
Figures 3, 15:
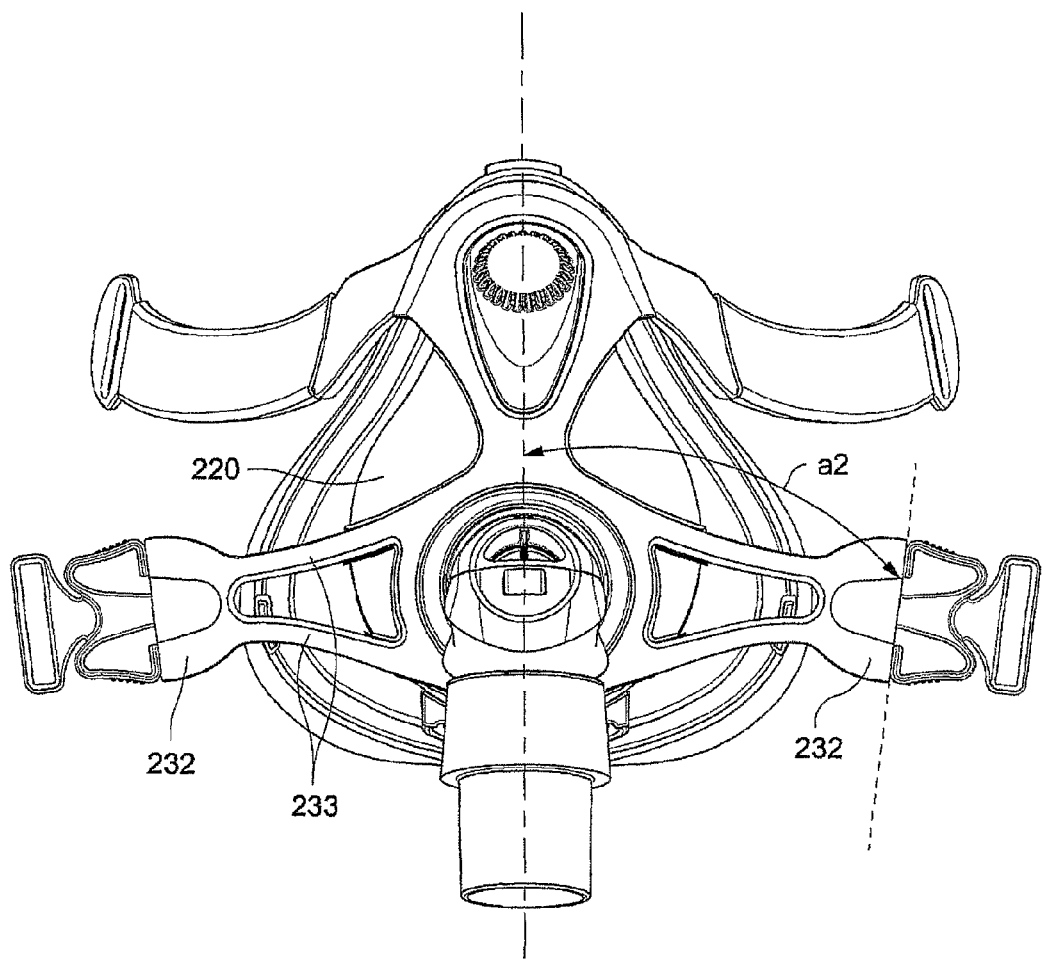
Figures 4, 15:
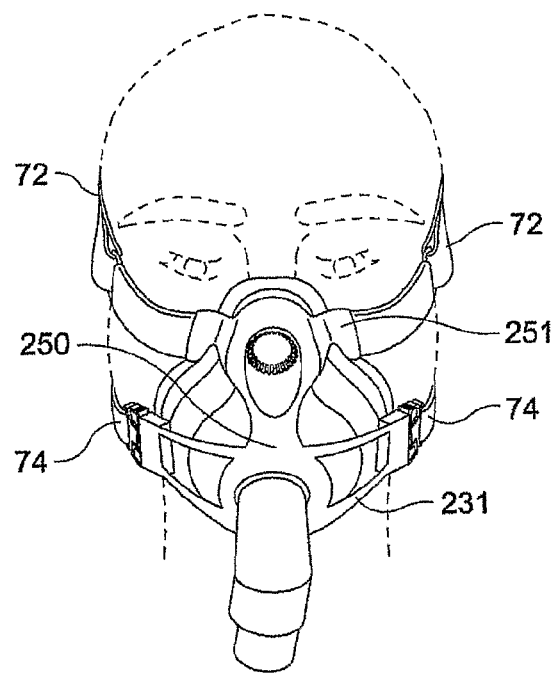
Figures 5, 15:
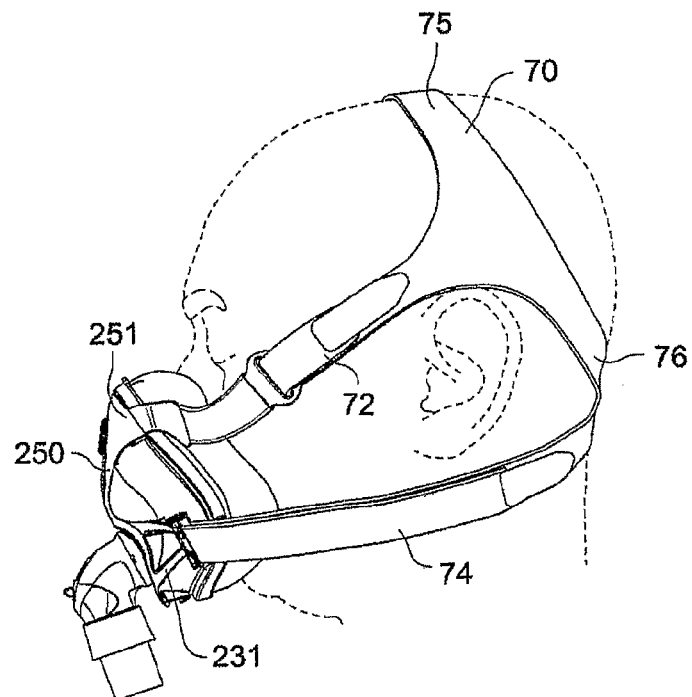

As illustrated, the top end of the shroud 250 is adapted to be positioned proximal to the nasal bridge region or nose of the patient and the bottom end is adapted to be positioned proximal to the mouth or chin of the patient (e.g., see FIGS. 15-4 and 15-5). The top end of the shroud includes an opening or vent receiving hole 258 to accommodate the vent arrangement 280 provided to the frame, and the bottom end includes an opening or elbow hole 259 to accommodate the elbow 260.

The upper headgear connectors 251 extend from each side of the top end, and the lower headgear connectors 231 extend from each side of the lower end. The headgear connectors 251, 231 may be integrally molded or otherwise attached to the shroud.

Each upper headgear connector 251 includes a curved arm 254 and a slot or receiving hole 255 as described above. The hole 255 may alternately be replaced with a series or plurality of holes to provide for increased adjustability.

Each lower headgear connector 231 includes a clip receptacle 232 adapted to be removably interlocked with a headgear clip 234 associated with a respective headgear strap. Each clip receptacle 232 is connected to the shroud via spaced-apart arm members 233, e.g., "wishbone" connection. As shown in FIGS. 15-1 to 15-3, the shroud 250 is molded such that the arm members 233 support the clip receptacles 232 in a raised or spaced position with respect to the frame 220 when no headgear tension is applied. Upon the application of headgear tension, the arm members 233 allow the clip receptacles 232 to flex towards and into contact with the frame 220 in use, e.g., to position the force vectors. FIGS. 15-4 and 15-5 show the mask system 210 in position on the patient's head in use.

FIGS. 15-2 and 15-3 show exemplary angles/force vectors provided by the clip receptacles when the mask system is worn by the patient. It is noted that such angles/force vectors may be consistent across all sizes of the shroud, e.g., small, medium, and large. In the embodiment shown in FIGS. 15-2 and 15-3, a1 may be about 40-50°, e.g., 45°, and a2 may be about 2-12°, e.g., 7°. However, other dimensions are possible.

Also, it is noted that the upper headgear connector 251 of the shroud 250 may include similar dimensions as described above with respect to the embodiment of the upper headgear connector 50 of FIGS. 9-1 to 9-6, for small, medium, and large sizes.

1.2.4 Arm Padding

In an embodiment, the arms 54, 254 may be used to stabilize the mask system by contacting the patient's face at the cheeks. As shown in FIGS. 1-1 to 2-2 and 12-1 to 12-4, the arms 54, 254 of the upper connectors 50, 251 may be enveloped in a soft fabric sleeve or padded material 90 to act as padding against the cheeks of the patient, e.g., for patient facial comfort. The soft fabric sleeve 90 may be in the configuration of an elastic tube or sock covering a portion of the arms.

Figures 1, 14:
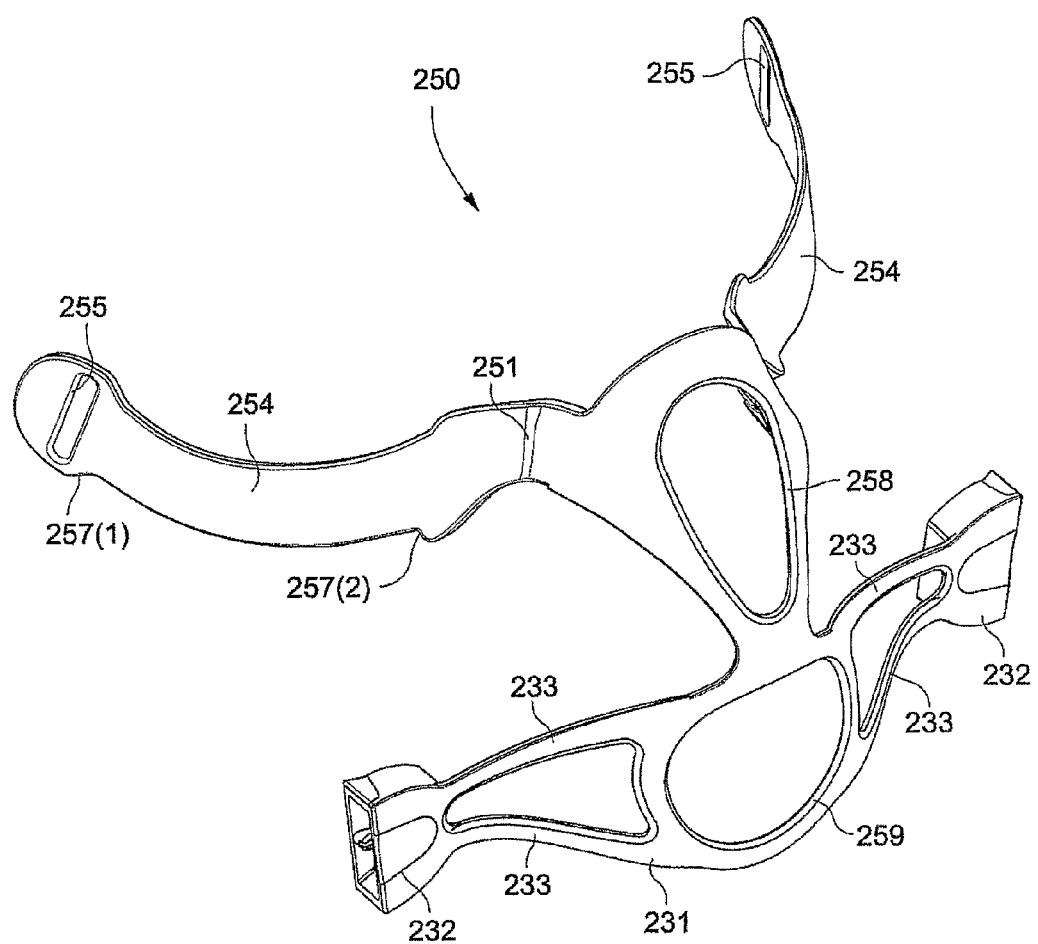
Figures 2, 14:
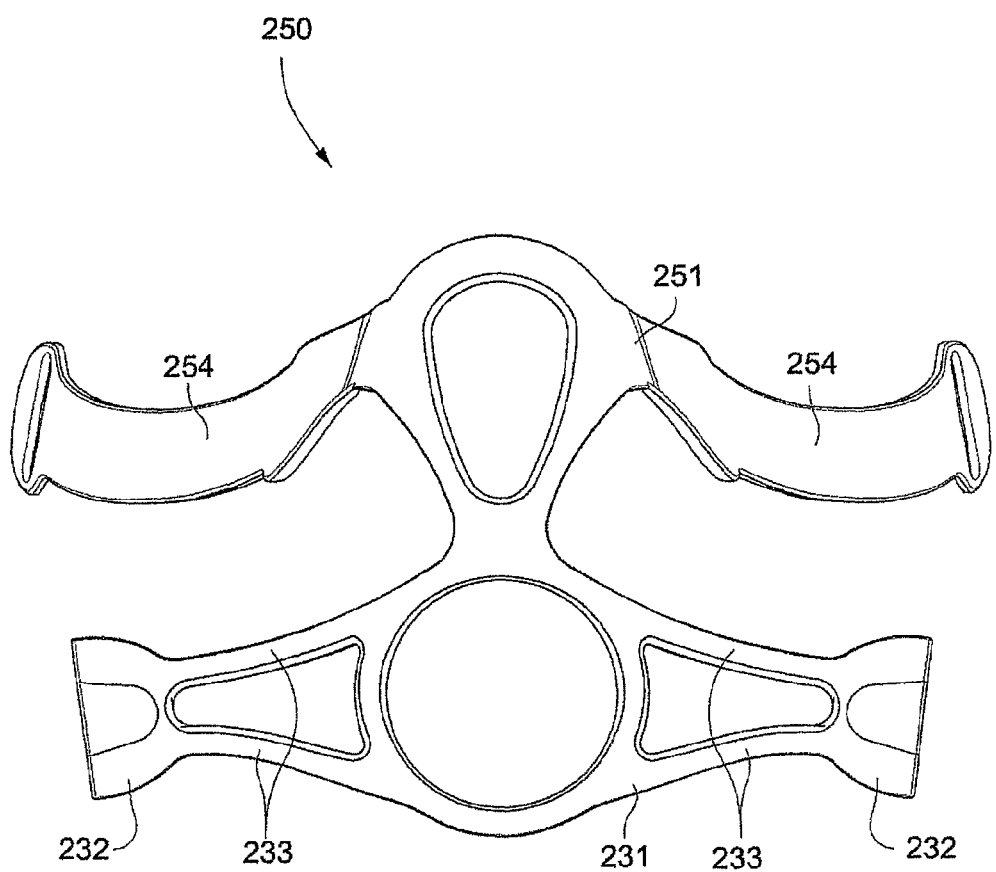
Figures 3, 14:
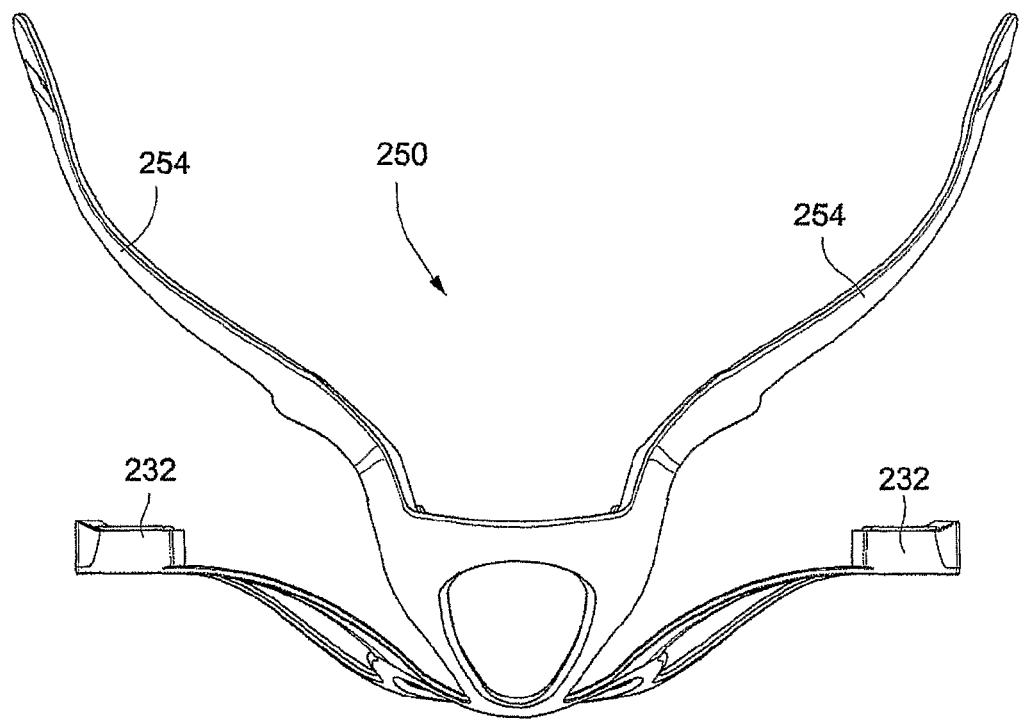
Figures 4, 14:
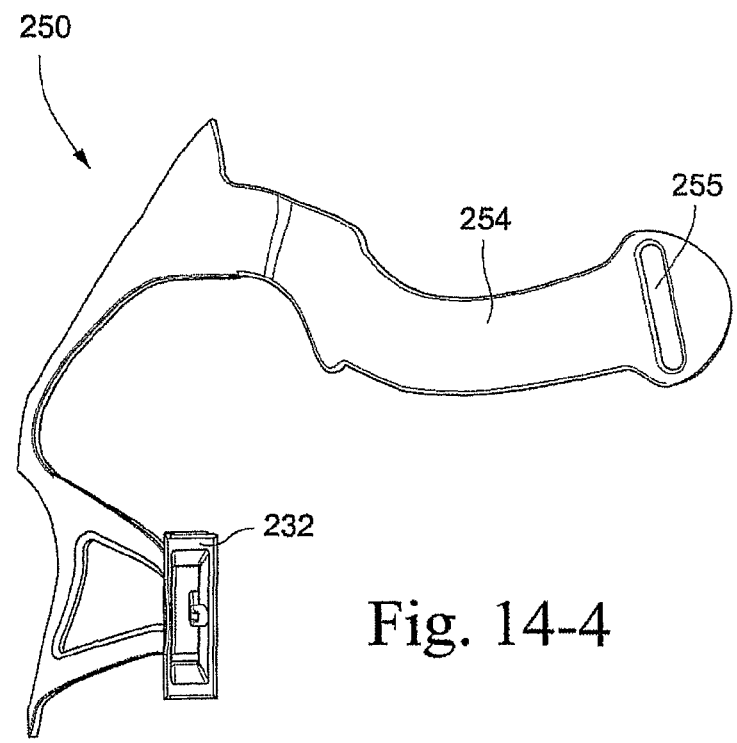

Also, the arms 54, 254 may be structured to retain the sleeve 90 thereon, e.g., prevent relative movement between the sleeve and arm. For example, as shown in FIGS. 14-1 to 14-4, the distal end of the arm (providing the slot) includes an enlarged head which provides a shoulder 257(1) for retaining an end of the sleeve. In addition, the proximal end of the arm includes a widened portion which provides a shoulder 257(2) for retaining the other end of the sleeve.

1.3 Headgear

Headgear may be removably attached to the headgear connectors to maintain the mask system in a desired position on the patient's face.

As shown in FIGS. 1-1 and 1-2, the headgear 70 includes a pair of upper straps 72 and a pair of lower straps 74 with the upper straps 72 removably attached to respective upper headgear connectors 50 and the lower straps 74 removably attached to respective lower headgear connectors 30. The free end of each strap 72, 74 may include a Velcro® tab structured to engage the remainder of the strap to secure the strap in place. Such Velcro® attachment also allows adjustment of the length of the straps. However, the upper and lower headgear straps may be secured to the headgear connectors in any other suitable manners, e.g., adjustable ladder-lock arrangement, etc.

The upper straps 72 split at the crown of the patient's head to a top strap 75 adapted to pass over the top of the patient's head in use and a rear strap 76 adapted to pass behind the patient's head in use. Such arrangement may help to realign the upper headgear vectors to prevent the mask system from sliding up the patient's face in use.

FIGS. 15-4 and 15-5 illustrate similar headgear 70 attached to the headgear connectors 251, 231 of the shroud 250 of mask system 210.

FIGS. 11-1 and 11-2 illustrate headgear according to an alternative embodiment. In this embodiment, a cross bar or connecting member 78 is provided to connect the upper and lower straps 72, 74. As illustrated, the connecting member 78 extends generally vertically in front the patient's ear and close to the patient's cheek in use. The connecting member 78 assists with headgear vectoring. For example, the upper strap 72 runs horizontally across the patient's cheeks to avoid obstructing the patient's eyes and to pull the mask directly onto the patient's face to get the mask to seal, and then the top strap turns upwards over the patient's ears to secure the mask on the patient's head without contacting the ears (which can be uncomfortable) and also pulls the mask upwards to prevent it from slipping down. The connecting member 78 limits relative movement of the upper and lower straps relative one another to maintain the positioning and alignment of the upper and lower straps 72, 74 to enhance alignment of the vectors for sealing.

Preferably, the cross bar 78 joins the upper and lower straps and maintains the upper strap in a position away from the field of vision of the patient. Additionally, the cross bar may alter the force vectors applied by the headgear to the mask system, by allowing the force vectors to applied to both the upper and lower straps in the same general direction towards the back of the patients head, when in use. Preferably, the cross bar may be adapted as such to allow the upper and lower strap to presented in a generally parallel alignment with each other. It is noted that the cross bar may not extend generally vertically, i.e., other configurations are possible.

Additionally, the cross bar may be elastic and flexible and be constructed of a similar material as to the other portions of the headgear and straps.

In alternative embodiments, the straps of the headgear may be able to connect directly to the frame through integrally molded loops, holes or apertures. Also, the headgear may include a strap constructed of multiple interlocking hook and loop (e.g., Velcro™) arrangements. The corresponding hook and loop pieces may be joined and aligned in a strap configuration, which may allow the user or patient to quickly and easily release the strap by separation of the hook and loop interlocking layers. This may serve as a quick release mechanism.

1.4 Cushion

The cushion 40 is structured to interface with the frame and form a seal with the patient's nose and mouth in use. In the illustrated embodiment, the cushion is a full-face cushion adapted to engage the patient's face generally along nasal bridge, cheek, and lower lip/chin regions of the patient's face. However, other cushion interfaces are possible, e.g., nasal.

The cushion may include a two or more wall configuration wherein the cushion comprises membrane and one or more undercushions or support walls underneath the membrane.

1.5 Elbow

As shown in FIG. 1-1 for example, the elbow 60 includes a first end portion providing an interfacing structure structured to interface or otherwise attach to the frame 20 and a second end portion including a swivel joint 62 is adapted to be connected to an air delivery tube.

1.5.1 AAV

The elbow is structured to support an anti-asphyxia valve (AAV), which includes a flap portion adapted to selectively close a port 64 on the elbow (depending on the presence of pressurized gas).

Alternative embodiments of the AAV are disclosed in PCT Application No. PCT/AU2006/000031, which is incorporated herein by reference in its entirety.

1.6 Shroud to Frame Connection

The shroud is mounted on the outer surface of the frame, e.g., preferably with a tight, conforming fit on the frame.

1.6.1 Retaining Mechanism

In the illustrated embodiment of FIGS. 1-1 to 3-2, the upper headgear rigidizer 50 is connected to the frame 20 by a retaining mechanism or interfacing structure located on the top end of the frame.

The retaining mechanism includes a taper lock arrangement and a retaining clip arrangement. In addition, an alignment feature is provided to facilitate alignment and connection of the upper headgear rigidizer to the frame.

As best shown in FIGS. 4-1 to 4-4 and 10-2, opposing sides of the top end of the frame include a platform 24 which provides a first female slot 25(1). In addition, the space between the platform 24 and the outer surface of the frame 20 defines a second female slot 25(2). As best shown in FIGS. 6-1 to 6-3 and 10-3, opposing sides of the frame connecting portion 52 of the upper headgear rigidizer 50 include a tang protrusion 53 on the underside thereof. The tang protrusion 53 includes a first tang 53(1) and a second tang 53(2) that extends generally transverse to the first tang. Each tang may taper along its length, i.e., thinner towards its free end.

Figures 1, 10:
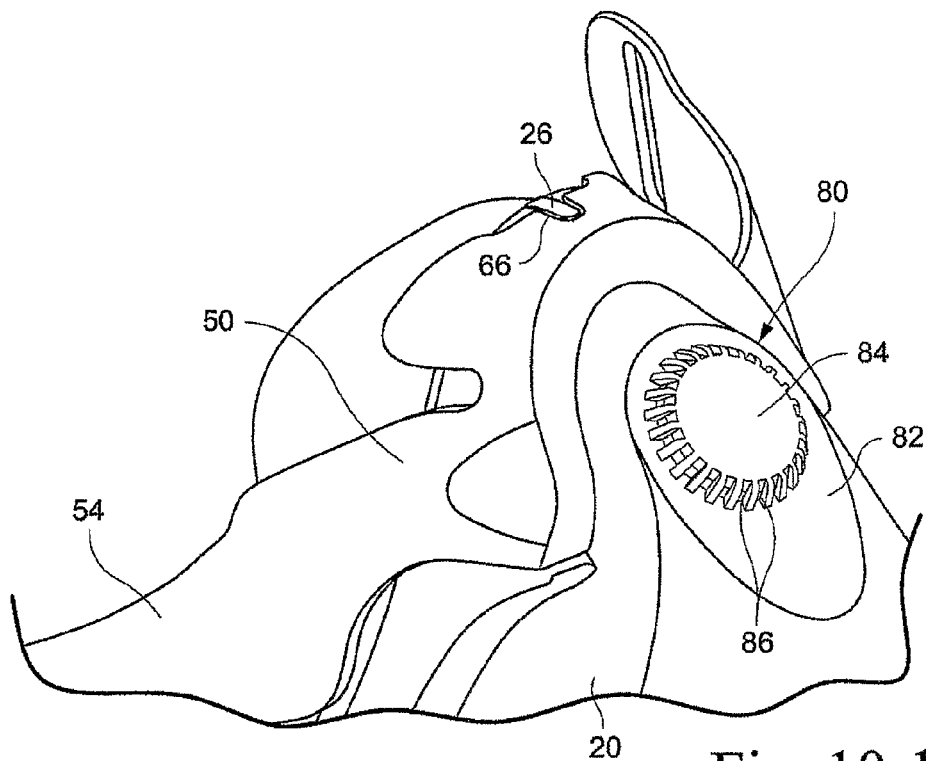
Figures 2, 10:
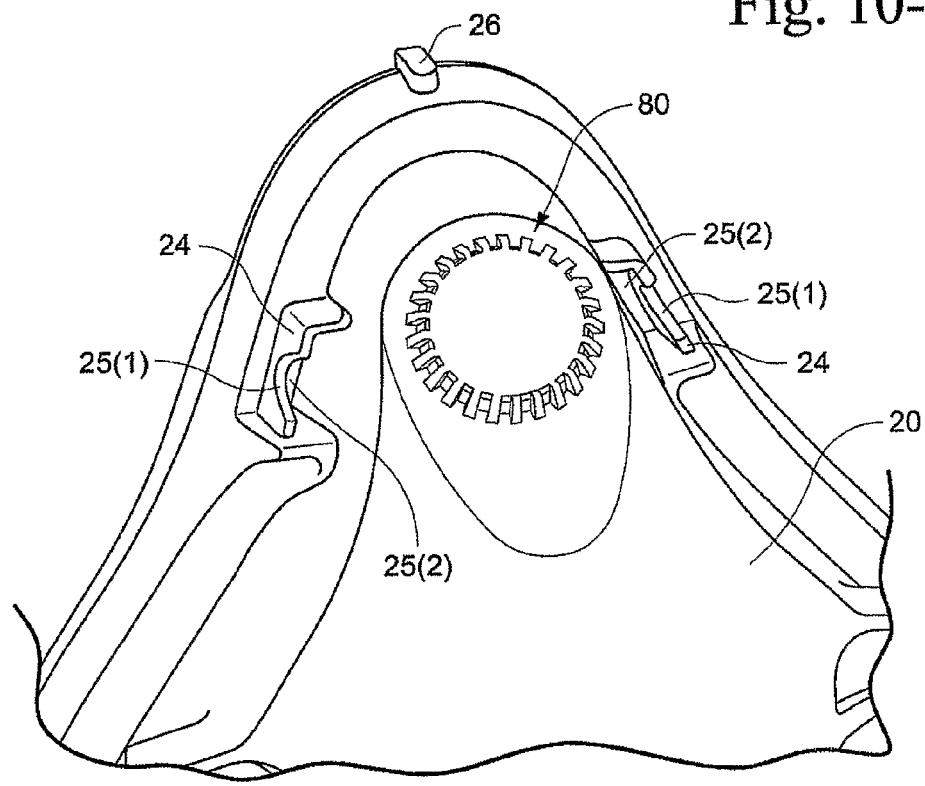
Figures 3, 10:
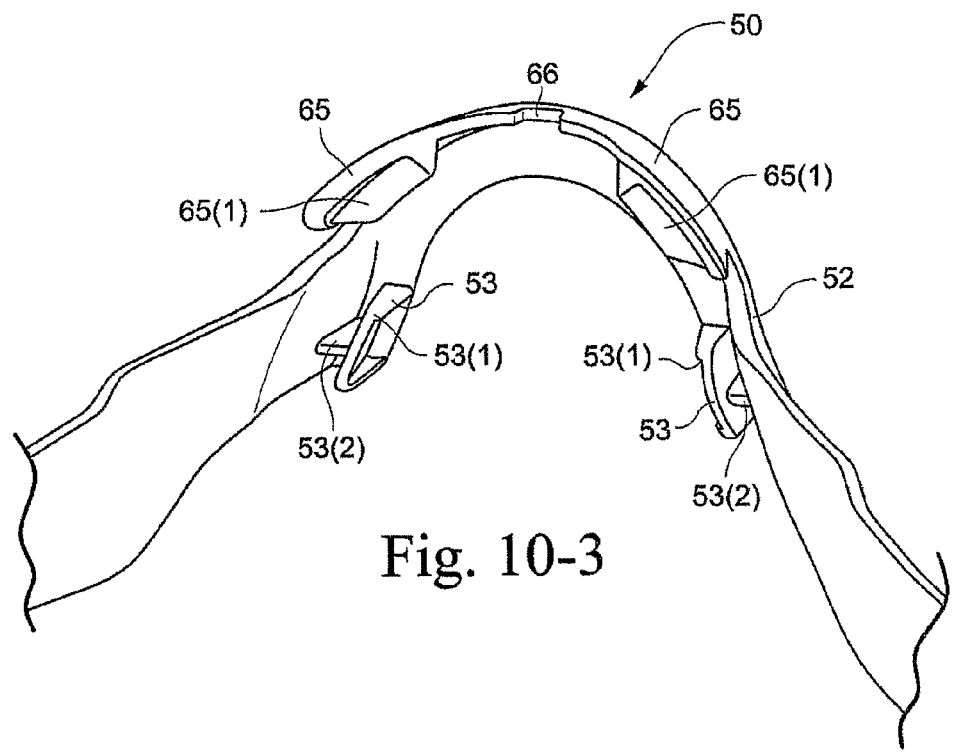
Figures 4, 10:
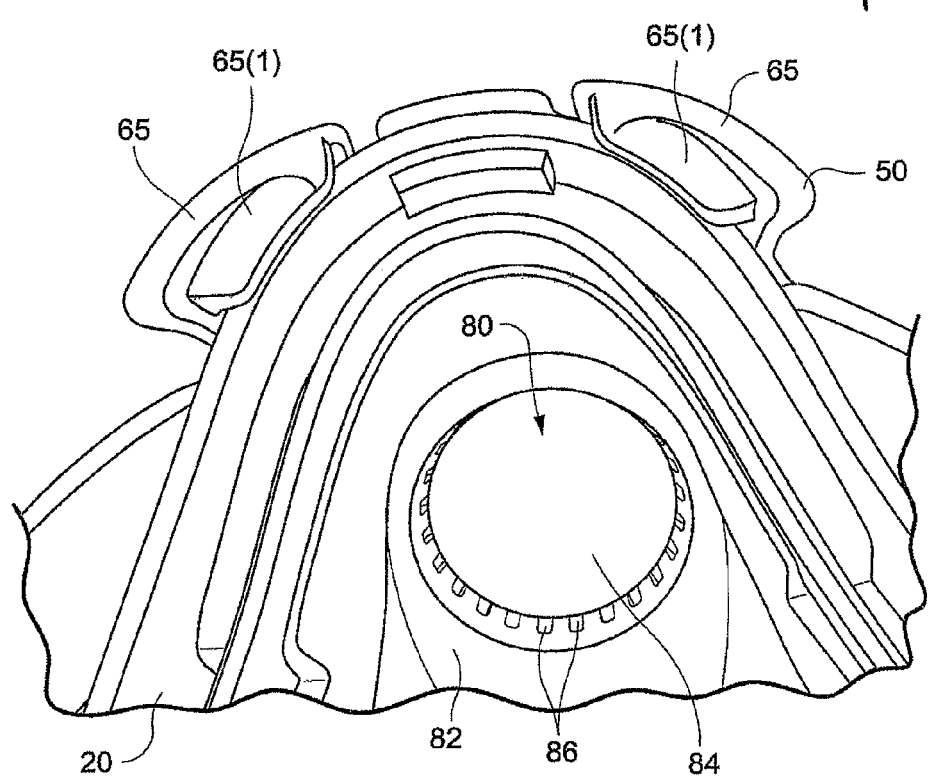
Figures 5, 10:
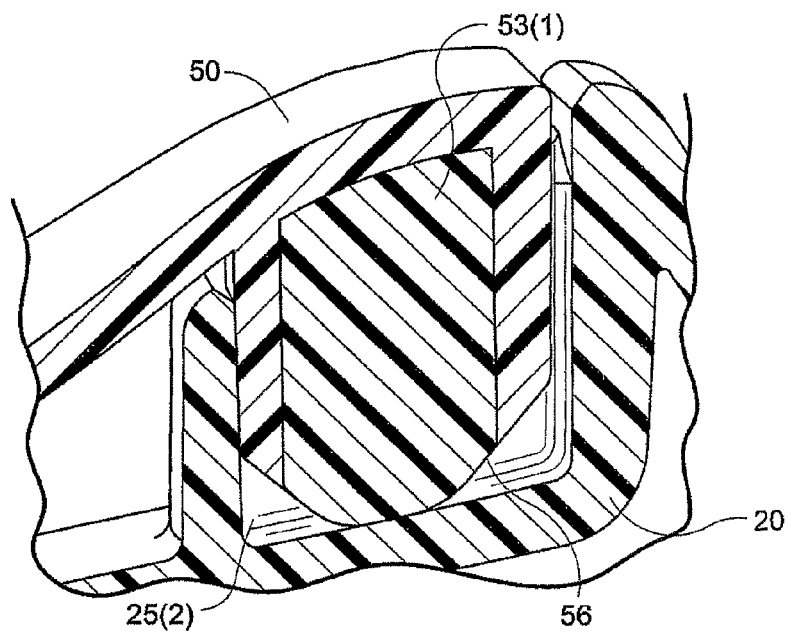
Figures 6, 10:
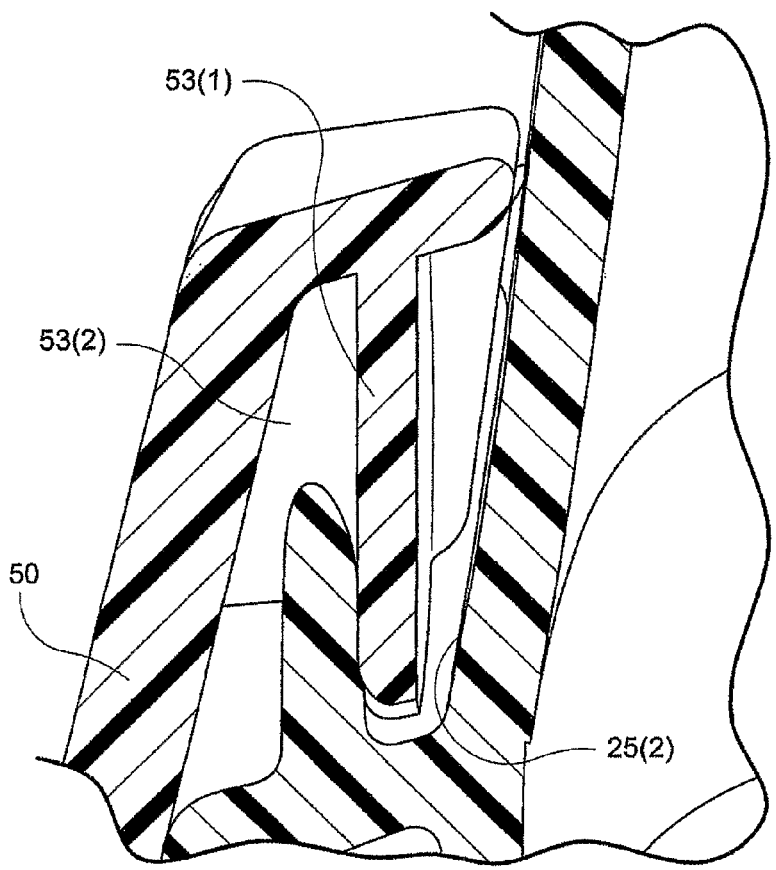
Figures 7, 10:
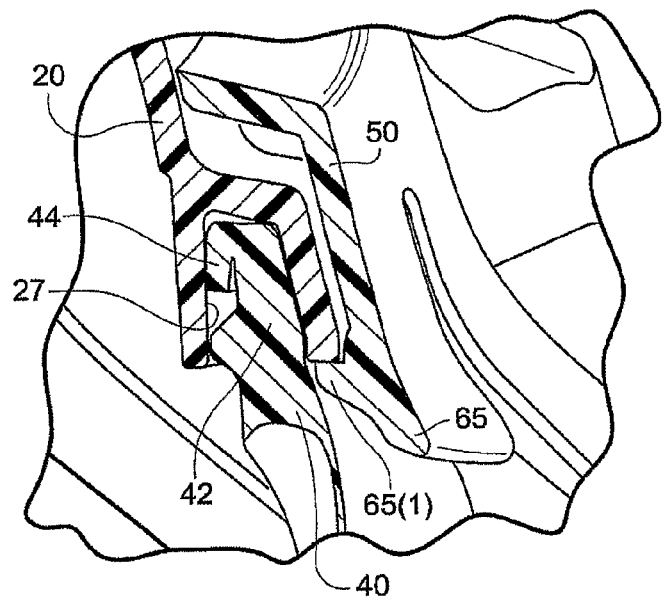

As shown in FIGS. 10-5 and 10-6, the tangs 53(1), 53(2) of each tang protrusion 53 are structured to engage with respective slots 25(2), 25(1). As best shown in FIG. 10-5, the tang 53(1) may include lead-ins or guides 56 that curve along their length so as to guide the tang into the slot and aid assembly.

As best shown in FIGS. 6-1 to 6-3 and 10-3, the upper portion of the frame connecting portion 52 includes a pair of spaced apart clip arms 65 with a locking tab 65(1) provided to each clip arm. In use, each clip arm is adapted to clip onto or overhang the edge of the frame 20, e.g., with a snap-fit, as shown in FIGS. 3-2, 10-4, and 10-7.

Specifically, the clip arms are adapted to engage the frame as the taper locks are progressively engaged. In an embodiment, the clip arms may provide an audible click once clipped onto the frame to indicate or confirm correct assembly.

In the illustrated embodiment, as best shown in FIGS. 10-1 to 10-3, the alignment feature includes a tab 26 provided to the frame and a slot 66 provided to the upper headgear rigidizer 50 and adapted to receive the tab 26 therein when the upper headgear rigidizer is engaged with the frame. However, other alignment features are possible, e.g., one or more alignment markings.

Figures 1, 7:
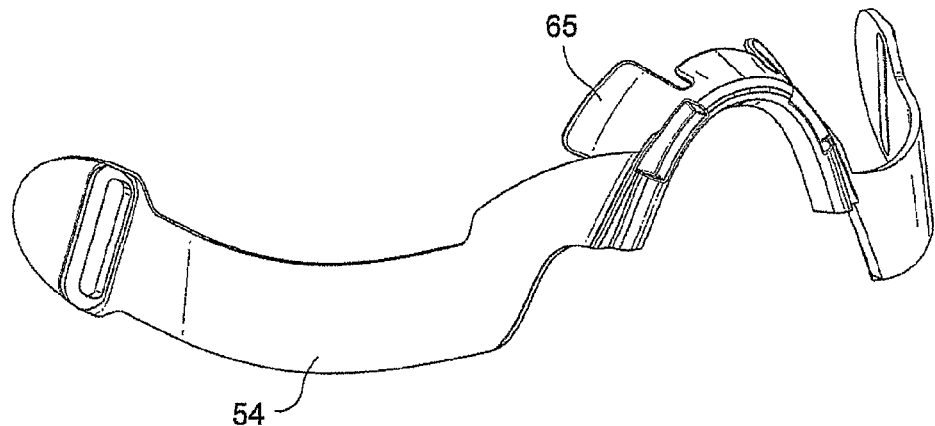
Figures 2, 7:
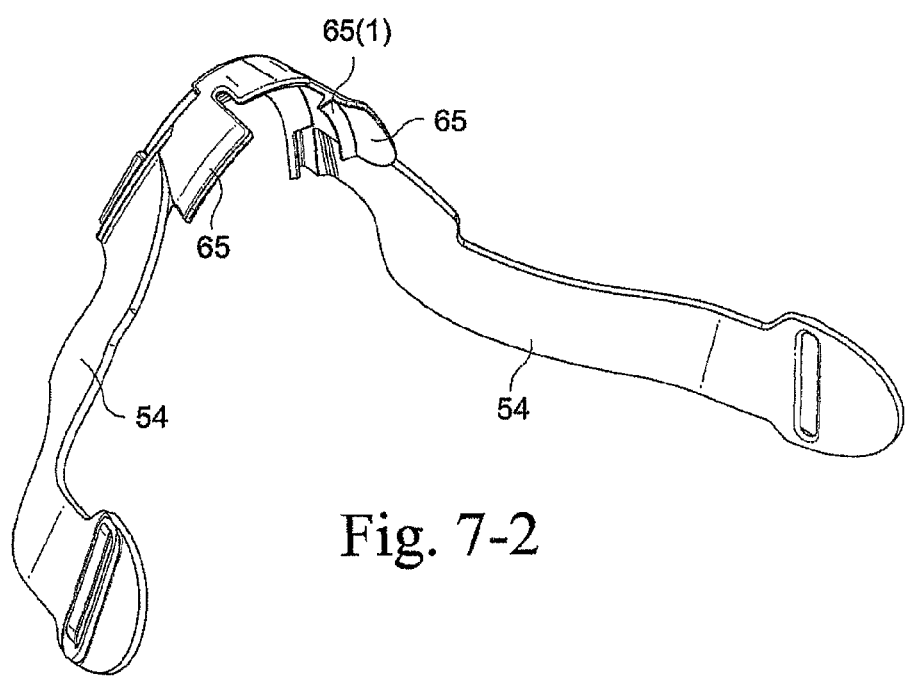
Figures 3, 7:
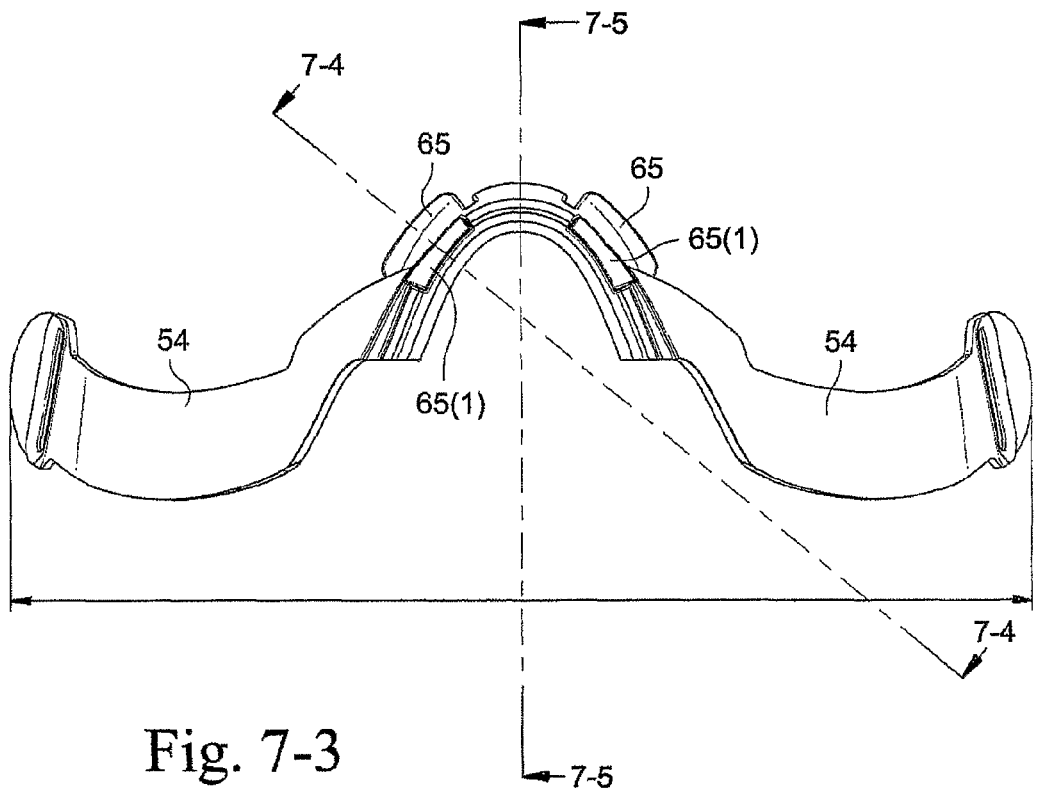
Figures 4, 7:
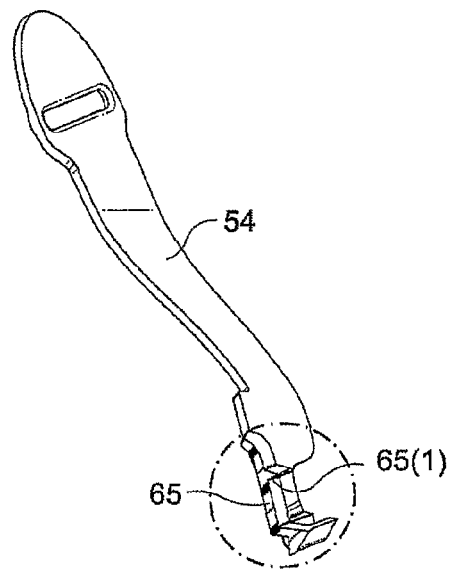
Figures 5, 7:
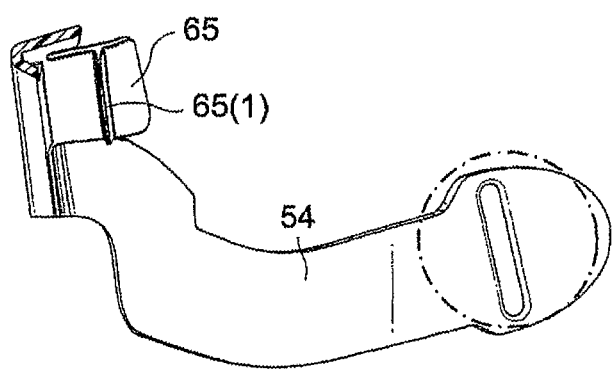

FIGS. 7-1 to 7-5 show an upper headgear rigidizer 50 according to an alternative embodiment. In this embodiment, the retaining mechanism only includes the retaining clip arrangement, i.e., no taper lock.

Figures 1, 12:
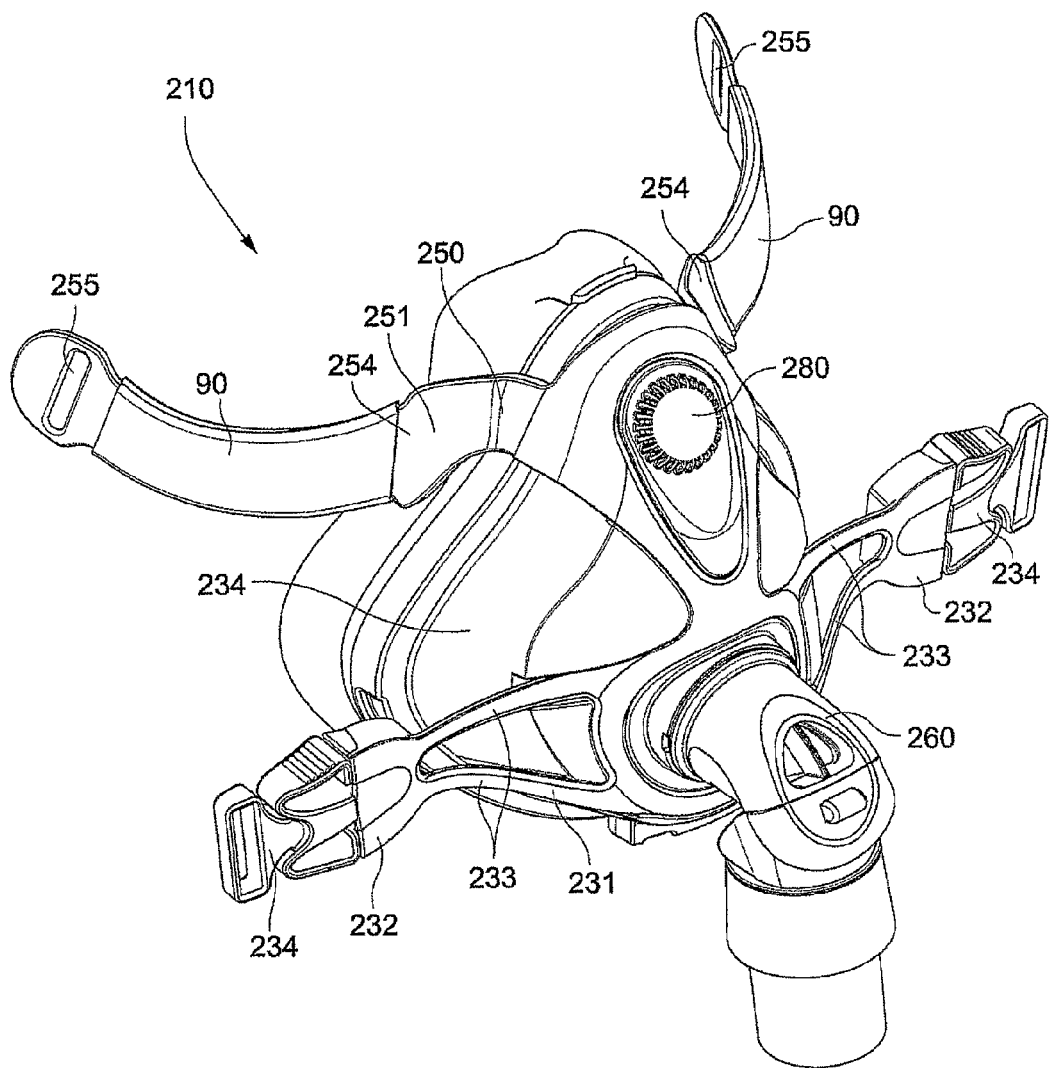
Figures 2, 12:
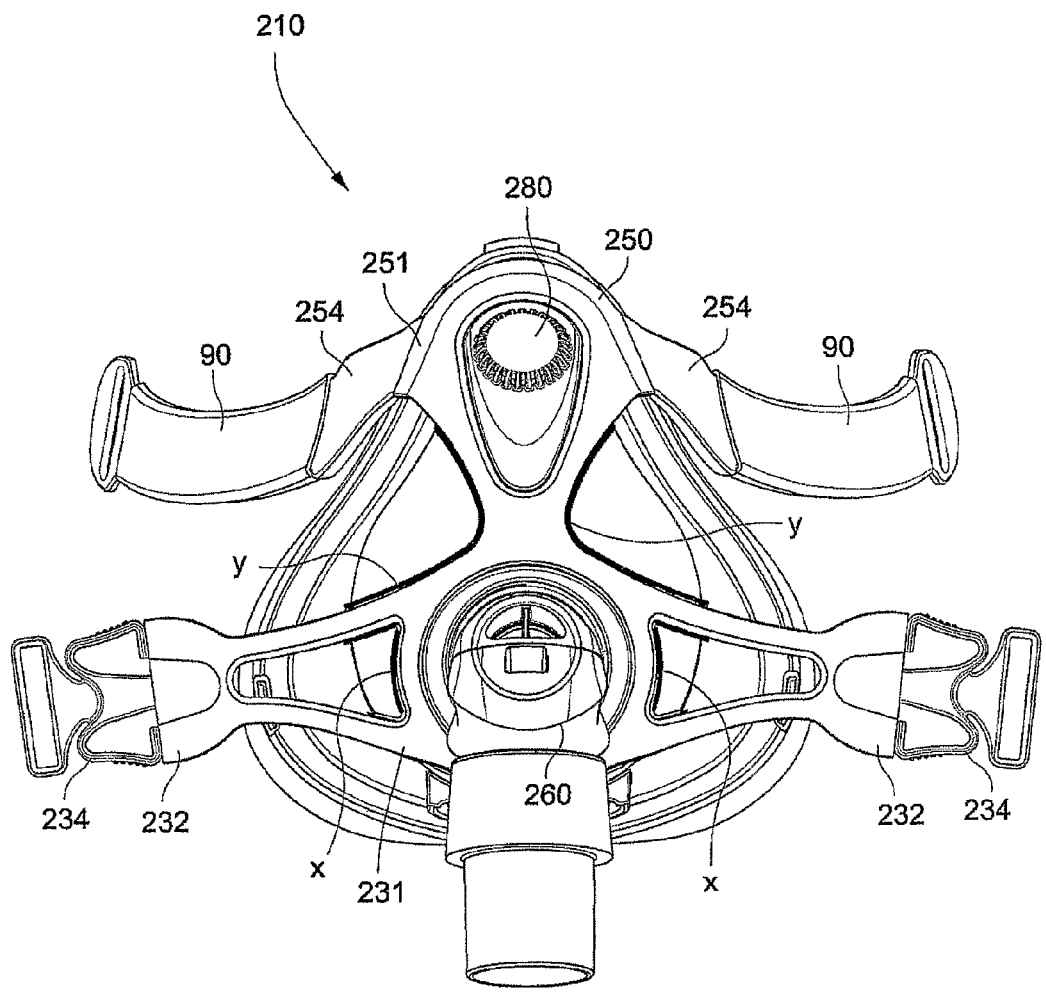
Figures 3, 12:
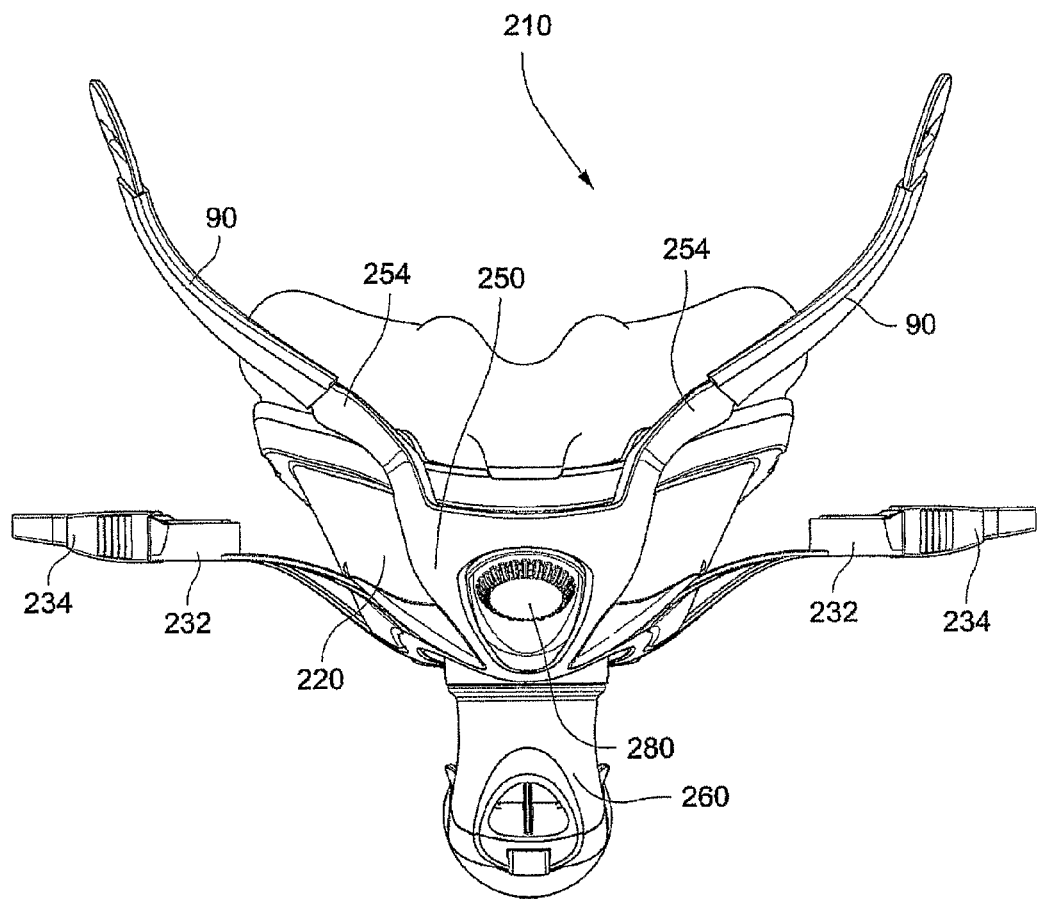
Figures 4, 12:
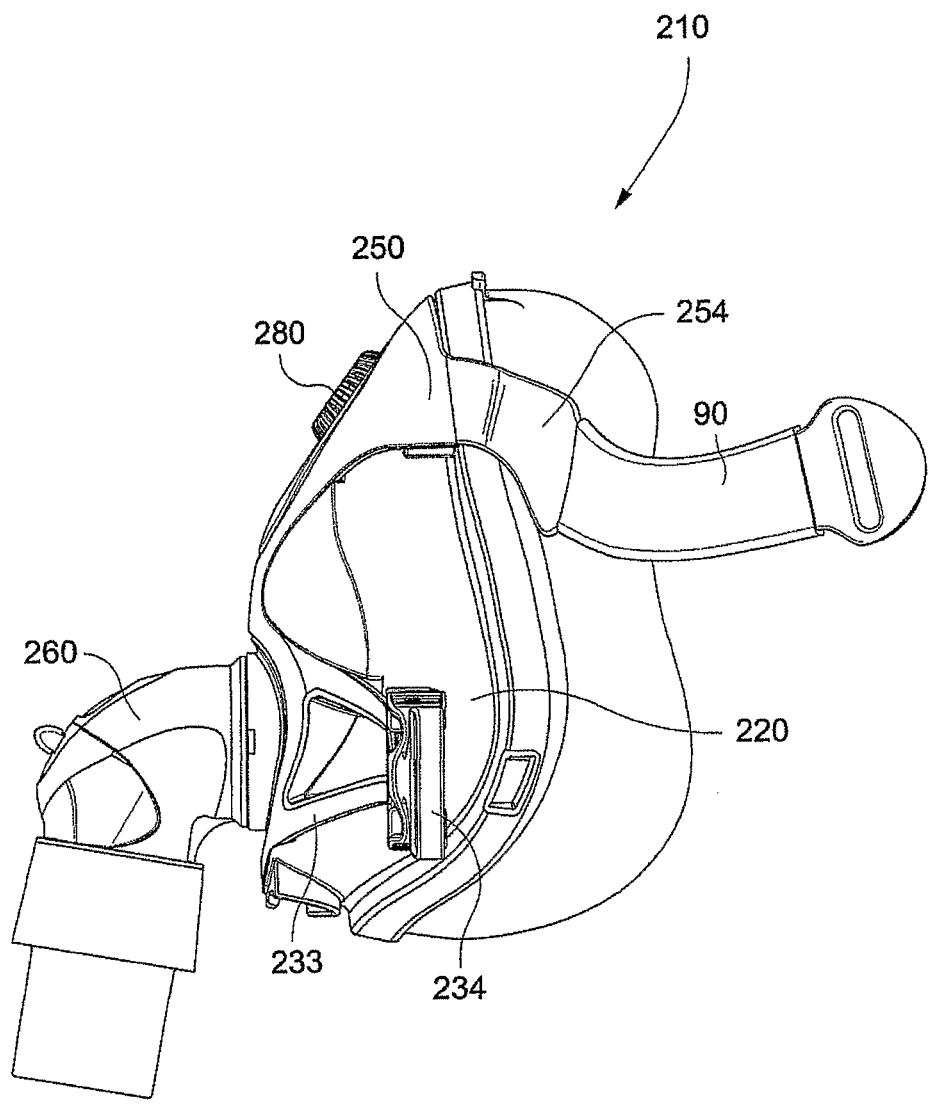

In the embodiment of FIG. 12-1, the top end of the shroud 250 may be connected to the frame using a taper lock arrangement and/or a retaining clip arrangement as described above.

1.6.2 Lower Retaining Mechanism

The lower end of the shroud 250 and frame 220 includes a lower retaining mechanism to connect the lower end of the shroud to the frame. In the illustrated embodiment, as shown in FIG. 16-1, the lower end of the shroud 250 includes a lug protrusion 268 adapted to mate into a corresponding recess or undercut 228 provided to the frame 220 so as to retain the shroud 250 in position. As illustrated, the lug protrusion 268 is in the form of a short bump that protrudes outwardly along a length of the shroud edge. For example, the protrusion 268 may extend along edges "x" of the shroud 250, and/or the protrusion 268 may extend along edges "y" of the shroud 250 as shown in FIG. 12-2.

Figures 1, 16:
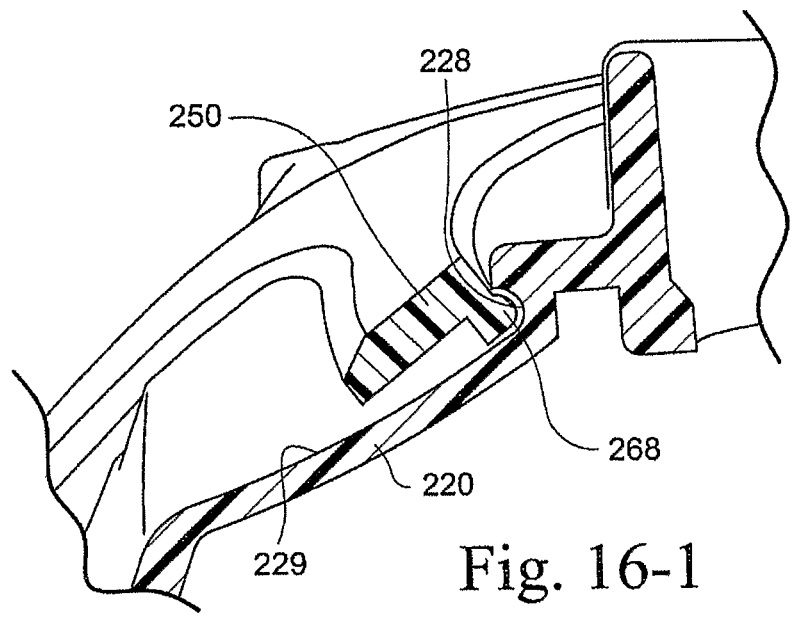
Figures 2, 16:
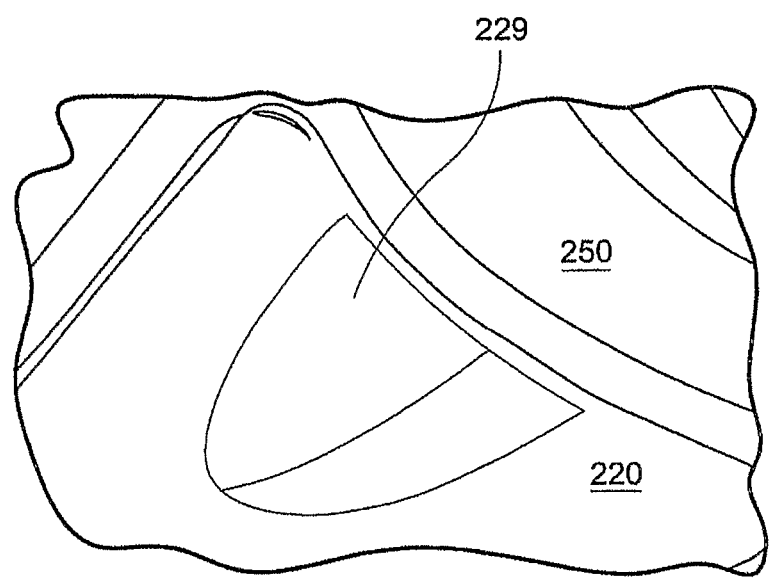

As shown in FIGS. 16-1 and 16-2, the outer surface of the frame 220 may include a recessed portion or scalloping 229 near the retention feature, which provides a finger grip to allow the patient an improved ability to grip the shroud 250 and disengage the retention feature when disengaging the shroud from the frame.

1.7 Cushion to Frame Connection

As best shown in FIG. 10-7, the non-face contacting side of the cushion 40 is connected to frame 20 in a tongue and groove relationship. The tongue 42 of the cushion 40 is inserted within a groove 27 provided along the perimeter of the frame 20. The tongue and groove relationship may also include a locking lip or sealing lip 44 on the cushion 40.

1.8 Ports

Figures 1, 13:
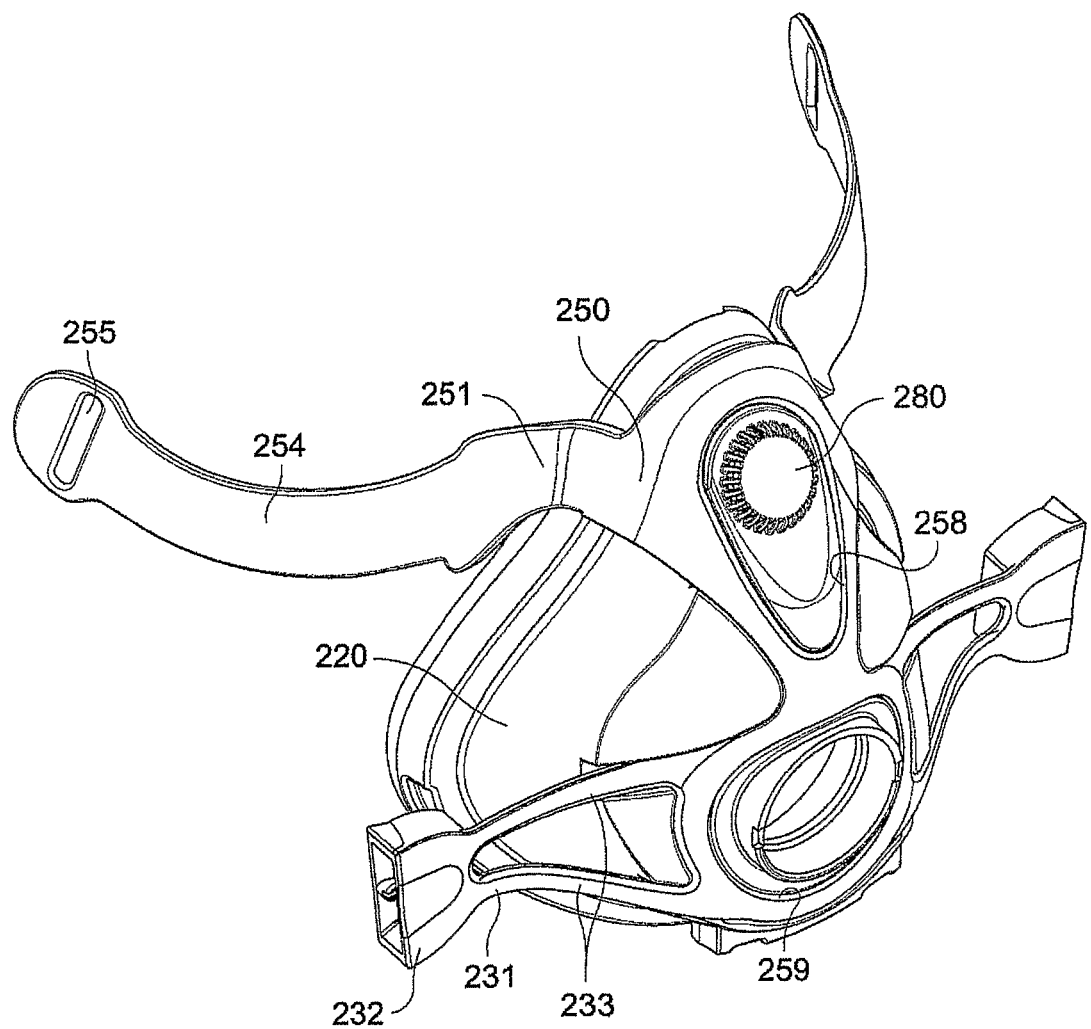
Figures 2, 13:
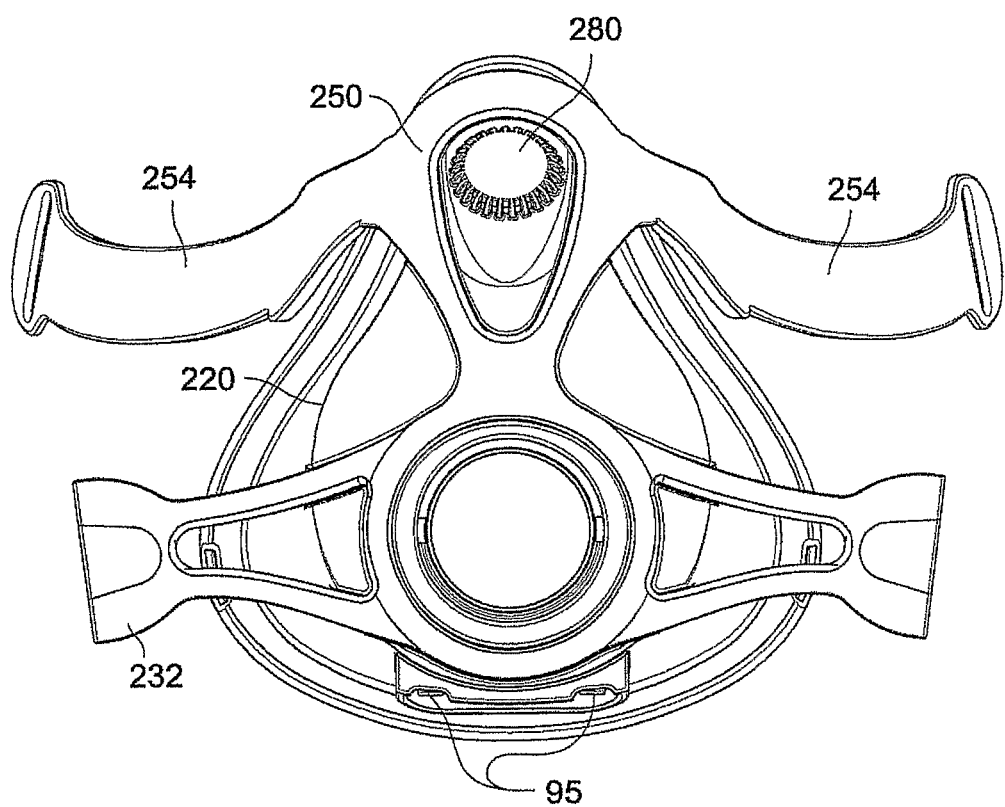
Figures 3, 13:
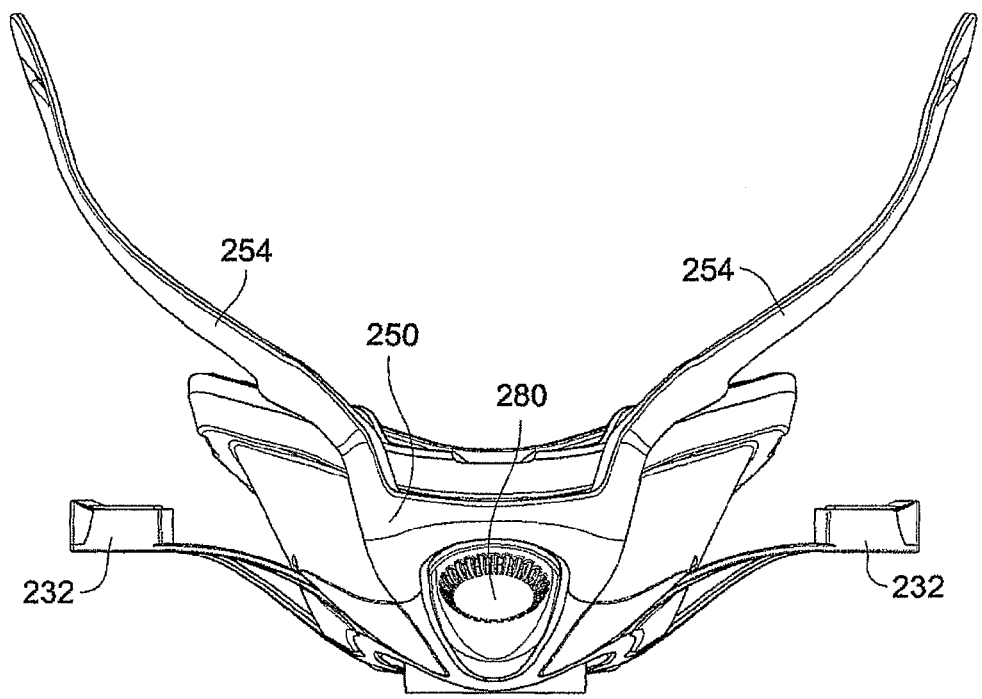
Figures 4, 13:
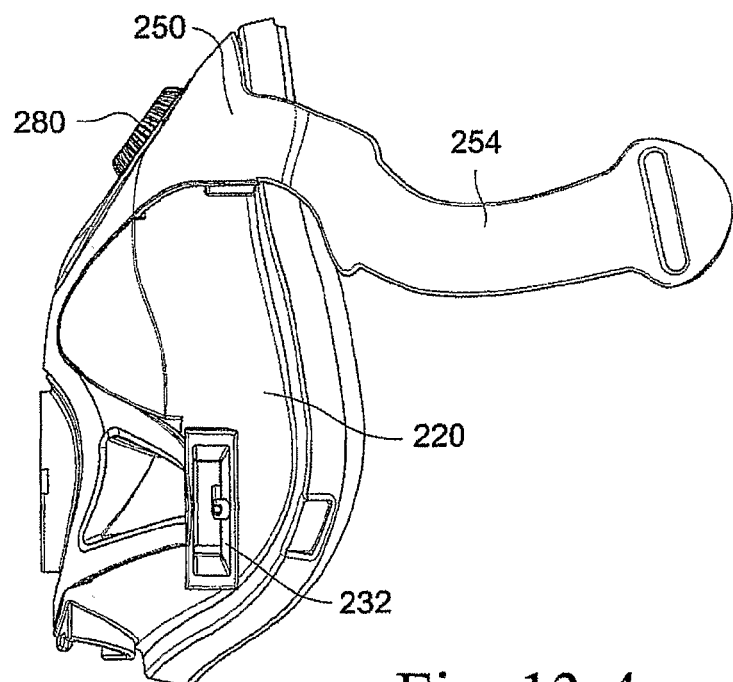

As best shown in FIG. 13-2, the base of the frame may includes two ports 95 positioned so that in use, oxygen or other breathable gas can be delivered close to the patient's nares or pressure monitoring equipment can be attached. The ports may also be used to attach additional medical equipment such as pressure or flow sensors. The ports may be selectively closable or sealable by a ports cap.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system comprising:
    a frame defining a breathing chamber;
    a cushion provided to the frame and configured to form a seal with a patient's face; and
    a shroud provided to the frame and configured to attach headgear,
    wherein the shroud includes a retaining mechanism structured to connect the shroud to the frame, the retaining mechanism includes both a taper lock arrangement that engages the frame and a retaining clip arrangement that engages the frame, and the taper lock arrangement includes a pair of tang protrusions provided on an underside of the shroud configured to engage with respective slots provided to the frame.

2. A mask system according to claim 1, wherein retaining clip arrangement includes a pair of spaced apart clip arms with a locking tab provided to each clip arm and configured to clip onto or overhang an edge of the frame.

3. A mask system according to claim 1, wherein the frame includes a tab and the shroud includes a slot configured to receive the tab therein when the shroud is connected to the frame so as to align the shroud with the frame.

4. A mask system according to claim 1, wherein the shroud includes upper headgear connectors configured to attach upper headgear straps, and the frame includes lower headgear connectors configured to attach lower headgear straps.

5. A mask system according to claim 4, wherein each upper headgear connector includes an elongated arm and a slot at a free end of the arm configured to receive a respective upper headgear strap.

6. A mask system according to claim 5, wherein each arm is enveloped in a soft fabric sleeve or padded material.

7. A mask system according to claim 1, wherein the shroud includes upper headgear connectors configured to attach upper headgear straps and lower headgear connectors configured to attach to lower headgear straps.

8. A mask system according to claim 7, wherein each lower headgear connector includes a clip receptacle configured to removably interlock with a headgear clip associated with a respective lower headgear strap.

9. A mask system according to claim 8, wherein each clip receptacle is connected to the shroud via spaced-apart arm members.

10. A mask system according to claim 1, wherein the shroud includes a second retaining mechanism structured to connect the shroud to a lower end of the frame.

11. A mask system according to claim 10, wherein the shroud includes a lug protrusion configured to mate into a corresponding recess or undercut provided to the frame so as to retain the shroud in position.

12. A mask system according to claim 11, wherein the lug protrusion is in the form of a short bump that protrudes outwardly along a length of an edge of the shroud.

13. A mask system according to claim 10, wherein the frame includes a recessed portion or scalloping near the second retaining mechanism.

14. A mask system according to claim 1, wherein the cushion is a full-face cushion.

15. A mask system according to claim 1, further comprising headgear, the headgear including at least a pair of upper straps, a pair of lower straps, and a cross bar to connect each pair of upper and lower straps, the cross bar configured to extend generally vertically in front the patient's ear in use.

16. A mask system according to claim 1, wherein the frame includes a vent arrangement for gas washout, the vent arrangement being in the form of a diffused vent cap including a base wall, a dome extending upwardly from the base above the horizontal surface of the base wall, and multiple vent holes arranged on an annular side wall of the dome.

17. A mask system according to claim 16, wherein the vent cap is integrally formed in one-piece with the frame.

18. A mask system according to claim 16, wherein the vent cap is structured to direct exhaust flow up and out from the mask system at an angle between about 0-30°.

19. A mask system according to claim 18, wherein the angle is about 20°.

20. A mask system according to claim 16, wherein the vent cap includes 25 vent holes.

21. A mask system according to claim 1, further comprising:
    upper headgear connectors configured to attach upper headgear straps and lower headgear connectors configured to attach lower headgear straps, each upper headgear connector includes an elongated arm and a slot at a free end of the arm configured to receive a respective upper headgear strap and each lower headgear connector includes a clip receptacle configured to removably interlock with a headgear clip associated with a respective lower headgear strap,
    wherein the slot is oriented about 2-26° with respect to a vertical axis of the frame.

22. A mask system according to claim 21, wherein the arms of the upper headgear connectors define an angle therebetween of about 56-112°.

23. A mask system according to claim 21, wherein the shroud includes the upper and/or lower headgear connectors.

24. A mask system according to claim 21, wherein at least a portion of each of the elongated arms are configured to be below a respective one of the patient's eyes.

25. A mask system according to claim 1,
    wherein the shroud includes upper headgear connectors configured to attach upper headgear straps and lower headgear connectors configured to attach lower headgear straps, each lower headgear connector including a clip receptacle configured to removably interlock with a headgear clip associated with a respective lower headgear strap, and wherein each clip receptacle is oriented about 2-12° with respect to a vertical axis of the frame.

26. A mask system according to claim 25, wherein the upper headgear connectors each include a portion that is configured to be below a respective one of the patient's eyes.

27. A mask system according to claim 1, wherein the retaining mechanism is structured to connect the shroud to an upper end of the frame.

28. A mask system according to claim 1, wherein
the frame includes a tab and the shroud includes a second slot configured to receive the tab therein when the shroud is connected to the frame so as to align the shroud with the frame.

29. A mask system according to claim 1, wherein each tang protrusion of the tang protrusions includes a first tang and a second tang that extends generally transverse to the first tang.

* * * * *